US009244523B2

(12) United States Patent
Ogawa et al.

(10) Patent No.: US 9,244,523 B2
(45) Date of Patent: Jan. 26, 2016

(54) MANIPULATOR SYSTEM

(71) Applicant: OLYMPUS CORPORATION, Tokyo (JP)

(72) Inventors: Ryohei Ogawa, Tokyo (JP); Masaru Yanagihara, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/169,321

(22) Filed: Jan. 31, 2014

(65) Prior Publication Data
US 2014/0148950 A1 May 29, 2014

Related U.S. Application Data

(63) Continuation of application No. PCT/JP2012/070417, filed on Aug. 3, 2012.

(60) Provisional application No. 61/515,203, filed on Aug. 4, 2011.

(30) Foreign Application Priority Data

May 22, 2012 (JP) ................................ 2012-116740

(51) Int. Cl.
G05B 19/04 (2006.01)
G05B 19/18 (2006.01)
(Continued)

(52) U.S. Cl.
CPC . G06F 3/01 (2013.01); A61B 17/29 (2013.01); A61B 17/32002 (2013.01);
(Continued)

(58) Field of Classification Search
CPC ............... A61B 19/2203; A61B 2019/2223; A61B 17/068; A61B 17/29; Y10S 901/08; Y10S 901/09; Y10S 901/30; G06F 3/01
USPC ............ 700/245, 249, 253, 257; 901/8, 9, 30
See application file for complete search history.

(56) References Cited

U.S. PATENT DOCUMENTS 3,139,990 A   7/1964 Jelatis et al.
4,830,569 A   5/1989 Jannborg
(Continued)

FOREIGN PATENT DOCUMENTS

CN   101027010 A   8/2007
CN   101167658 A   4/2008
(Continued)

OTHER PUBLICATIONS
English Abstract of JP 01-234140 dated Sep. 19, 1989.
(Continued)

Primary Examiner — Dalena Tran
Assistant Examiner — Jaime Figueroa
(74) Attorney, Agent, or Firm — Scully, Scott, Murphy & Presser, PC

(57) ABSTRACT

A manipulator system includes a master manipulation unit that performs a manipulation input by an operator, a slave motion unit that operates in accordance with the manipulation input, an interlock control unit that analyzes the manipulation input and performs control to operate the slave motion unit, interlocking with the manipulation input, and an interlock permission input unit that is capable of being manipulated by the operator and transmits, to the interlock control unit, an interlock permission mode signal used to enter a mode in which interlock of the slave motion unit is permitted based on the manipulation input of the mater manipulation unit when the operator manipulates the interlock permission input unit.

9 Claims, 10 Drawing Sheets

(51) Int. Cl.

| | | |
|---|---|---|
| *G06F 3/01* | (2006.01) | |
| *B25J 13/02* | (2006.01) | |
| *A61B 19/00* | (2006.01) | |
| *B25J 3/04* | (2006.01) | |
| *B25J 9/16* | (2006.01) | |
| *A61B 17/29* | (2006.01) | |
| *A61B 17/32* | (2006.01) | |
| *A61B 18/14* | (2006.01) | |
| *A61B 19/08* | (2006.01) | |
| *A61B 17/068* | (2006.01) | |
| *A61B 19/10* | (2006.01) | |
| *A61B 17/00* | (2006.01) | |

(52) U.S. Cl.
CPC .......... *A61B 18/1402* (2013.01); *A61B 19/081* (2013.01); *A61B 19/22* (2013.01); *A61B 19/2203* (2013.01); *A61B 19/26* (2013.01); *A61B 19/44* (2013.01); *B25J 3/04* (2013.01); *B25J 9/1689* (2013.01); *B25J 13/02* (2013.01); *A61B 17/068* (2013.01); *A61B 19/10* (2013.01); *A61B 19/5244* (2013.01); *A61B 19/56* (2013.01); *A61B 2017/00119* (2013.01); *A61B 2017/00477* (2013.01); *A61B 2017/00482* (2013.01); *A61B 2019/2223* (2013.01); *A61B 2019/2269* (2013.01); *A61B 2019/2292* (2013.01); *A61B 2019/2296* (2013.01); *A61B 2019/465* (2013.01); *A61B 2019/467* (2013.01); *A61B 2019/4815* (2013.01); *A61B 2019/4868* (2013.01); *A61B 2019/4873* (2013.01); *A61B 2019/5255* (2013.01); *A61B 2019/5289* (2013.01); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | | |
|---|---|---|---|
| 5,214,969 A | 6/1993 | Adkins et al. | |
| 5,603,723 A | 2/1997 | Aranyi et al. | |
| 5,632,432 A | 5/1997 | Schulze et al. | |
| 5,649,956 A | 7/1997 | Jensen et al. | |
| 5,656,903 A | 8/1997 | Shui et al. | |
| 5,712,543 A | 1/1998 | Sjostrom | |
| 5,762,458 A * | 6/1998 | Wang et al. | 414/1 |
| 5,836,869 A | 11/1998 | Kudo et al. | |
| 5,855,583 A | 1/1999 | Wang et al. | |
| 5,871,493 A | 2/1999 | Sjostrom et al. | |
| 6,007,550 A | 12/1999 | Wang et al. | |
| 6,063,095 A | 5/2000 | Wang et al. | |
| 6,090,122 A | 7/2000 | Sjostrom et al. | |
| 6,102,850 A | 8/2000 | Wang et al. | |
| 6,132,368 A | 10/2000 | Cooper | |
| 6,132,441 A | 10/2000 | Grace | |
| 6,206,903 B1 | 3/2001 | Ramans | |
| 6,246,200 B1 | 6/2001 | Blumenkranz et al. | |
| 6,328,752 B1 | 12/2001 | Sjostrom et al. | |
| 6,346,072 B1 | 2/2002 | Cooper | |
| 6,430,473 B1 | 8/2002 | Lee et al. | |
| 6,436,107 B1 | 8/2002 | Wang et al. | |
| 6,441,577 B2 | 8/2002 | Blumenkranz et al. | |
| 6,557,558 B1 | 5/2003 | Tajima et al. | |
| 6,574,355 B2 | 6/2003 | Green | |
| 6,587,750 B2 | 7/2003 | Gerbi et al. | |
| 6,602,185 B1 | 8/2003 | Uchikubo | |
| 6,645,196 B1 | 11/2003 | Nixon et al. | |
| 6,666,876 B2 | 12/2003 | Kawai et al. | |
| 6,676,684 B1 | 1/2004 | Morley et al. | |
| 6,685,698 B2 | 2/2004 | Morley et al. | |
| 6,699,177 B1 | 3/2004 | Wang et al. | |
| 6,746,443 B1 | 6/2004 | Morley et al. | |
| 6,783,524 B2 | 8/2004 | Anderson et al. | |
| 6,786,896 B1 | 9/2004 | Madhani et al. | |
| 6,853,879 B2 * | 2/2005 | Sunaoshi | 700/253 |
| 6,866,671 B2 | 3/2005 | Tierney et al. | |
| 6,905,460 B2 | 6/2005 | Wang et al. | |
| 6,913,613 B2 | 7/2005 | Schwarz et al. | |
| 7,083,571 B2 | 8/2006 | Wang et al. | |
| 7,101,363 B2 | 9/2006 | Nishizawa et al. | |
| 7,107,124 B2 | 9/2006 | Green | |
| 7,118,582 B1 | 10/2006 | Wang et al. | |
| 7,273,488 B2 | 9/2007 | Nakamura et al. | |
| 7,295,893 B2 * | 11/2007 | Sunaoshi | 700/262 |
| 7,313,464 B1 | 12/2007 | Perreault et al. | |
| 7,331,967 B2 | 2/2008 | Lee et al. | |
| 7,357,774 B2 | 4/2008 | Cooper | |
| 7,373,219 B2 | 5/2008 | Nowlin et al. | |
| 7,422,592 B2 | 9/2008 | Morley et al. | |
| 7,476,237 B2 | 1/2009 | Taniguchi et al. | |
| 7,549,998 B2 | 6/2009 | Braun | |
| 7,608,083 B2 | 10/2009 | Lee et al. | |
| 7,654,431 B2 | 2/2010 | Hueil et al. | |
| 7,666,191 B2 | 2/2010 | Orban, III et al. | |
| 7,674,255 B2 | 3/2010 | Braun | |
| 7,695,481 B2 | 4/2010 | Wang et al. | |
| 7,699,835 B2 | 4/2010 | Lee et al. | |
| 7,699,855 B2 | 4/2010 | Anderson et al. | |
| 7,778,733 B2 | 8/2010 | Nowlin et al. | |
| 7,819,884 B2 | 10/2010 | Lee et al. | |
| 7,819,885 B2 | 10/2010 | Cooper | |
| 7,862,579 B2 | 1/2011 | Ortiz et al. | |
| 7,865,266 B2 | 1/2011 | Moll et al. | |
| 7,955,321 B2 | 6/2011 | Kishi et al. | |
| 8,105,320 B2 | 1/2012 | Manzo | |
| 8,155,479 B2 | 4/2012 | Hoffman et al. | |
| 8,267,958 B2 | 9/2012 | Braun | |
| 8,350,806 B2 | 1/2013 | Nagasaka et al. | |
| 8,423,186 B2 * | 4/2013 | Itkowitz et al. | 700/250 |
| 8,496,647 B2 | 7/2013 | Blumenkranz et al. | |
| 8,540,748 B2 | 9/2013 | Murphy et al. | |
| 8,845,681 B2 | 9/2014 | Grace | |
| 8,876,858 B2 | 11/2014 | Braun | |
| 8,903,549 B2 * | 12/2014 | Itkowitz et al. | 700/250 |
| 8,906,002 B2 | 12/2014 | Kishi et al. | |
| 2001/0021859 A1 | 9/2001 | Kawai et al. | |
| 2001/0055062 A1 | 12/2001 | Shioda et al. | |
| 2002/0072736 A1 | 6/2002 | Tierney et al. | |
| 2002/0091374 A1 | 7/2002 | Cooper | |
| 2002/0128552 A1 * | 9/2002 | Nowlin et al. | 600/427 |
| 2003/0033024 A1 * | 2/2003 | Sunaoshi | 700/3 |
| 2003/0060927 A1 | 3/2003 | Gerbi et al. | |
| 2003/0069471 A1 | 4/2003 | Nakanishi et al. | |
| 2003/0083648 A1 | 5/2003 | Wang et al. | |
| 2003/0100817 A1 | 5/2003 | Wang et al. | |
| 2003/0216723 A1 | 11/2003 | Shinmura et al. | |
| 2004/0092912 A1 | 5/2004 | Jinno et al. | |
| 2004/0111113 A1 | 6/2004 | Nakamura et al. | |
| 2004/0140787 A1 | 7/2004 | Okamoto et al. | |
| 2004/0186345 A1 | 9/2004 | Yang et al. | |
| 2004/0186624 A1 | 9/2004 | Oda et al. | |
| 2004/0243147 A1 | 12/2004 | Lipow | |
| 2005/0020876 A1 | 1/2005 | Shioda et al. | |
| 2005/0021050 A1 | 1/2005 | Cooper | |
| 2005/0033117 A1 | 2/2005 | Ozaki et al. | |
| 2005/0125027 A1 | 6/2005 | Knodel et al. | |
| 2005/0149003 A1 | 7/2005 | Tierney et al. | |
| 2005/0228365 A1 | 10/2005 | Wang et al. | |
| 2005/0273086 A1 | 12/2005 | Green et al. | |
| 2006/0052664 A1 | 3/2006 | Julian et al. | |
| 2006/0074408 A1 | 4/2006 | Jinno et al. | |
| 2006/0079865 A1 | 4/2006 | Jinno et al. | |
| 2006/0079866 A1 | 4/2006 | Jinno et al. | |
| 2006/0087746 A1 | 4/2006 | Lipow | |
| 2006/0116973 A1 | 6/2006 | Okamoto et al. | |
| 2006/0155262 A1 | 7/2006 | Kishi et al. | |
| 2006/0161138 A1 | 7/2006 | Orban, III et al. | |
| 2006/0190031 A1 | 8/2006 | Wales et al. | |
| 2006/0235436 A1 | 10/2006 | Anderson et al. | |
| 2007/0012135 A1 | 1/2007 | Tierney et al. | |
| 2007/0089557 A1 | 4/2007 | Solomon et al. | |
| 2007/0119274 A1 | 5/2007 | Devengenzo et al. | |

(56) References Cited

U.S. PATENT DOCUMENTS

| | | |
|---|---|---|
| 2007/0137372 A1 | 6/2007 | Devengenzo et al. |
| 2007/0138992 A1 | 6/2007 | Prisco et al. |
| 2007/0142825 A1 | 6/2007 | Prisco et al. |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1* | 7/2008 | Brock et al. ............ 606/130 |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0228264 A1 | 9/2010 | Robinson et al. |
| 2010/0228265 A1 | 9/2010 | Prisco |
| 2010/0234857 A1* | 9/2010 | Itkowitz et al. ............ 606/130 |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1* | 12/2010 | Itkowitz et al. ............ 700/245 |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | Van den Dool et al. |
| 2011/0230894 A1 | 9/2011 | Simaan et al. |
| 2011/0238079 A1 | 9/2011 | Hannaford et al. |
| 2011/0282493 A1 | 11/2011 | Ortmaier |
| 2011/0288579 A1 | 11/2011 | Hyodo |
| 2012/0071752 A1 | 3/2012 | Sewell et al. |
| 2012/0165828 A1 | 6/2012 | Duque et al. |
| 2012/0191245 A1 | 7/2012 | Fudaba et al. |

FOREIGN PATENT DOCUMENTS

| | | |
|---|---|---|
| CN | 101426412 A | 5/2009 |
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |
| EP | 2 298 220 A1 | 3/2011 |
| EP | 2 332 484 A2 | 6/2011 |
| JP | 63-029810 A | 2/1988 |
| JP | 64-034688 A | 2/1989 |
| JP | 01-271185 A | 10/1989 |
| JP | 02-071980 A | 3/1990 |
| JP | 02-292193 A | 12/1990 |
| JP | 03-161289 A | 7/1991 |
| JP | 05-096477 A | 4/1993 |
| JP | 5-329784 A | 12/1993 |
| JP | 07-001366 A | 1/1995 |
| JP | 07-194609 A | 8/1995 |
| JP | 07-241300 A | 9/1995 |
| JP | 07-246578 A | 9/1995 |
| JP | 07-096182 B2 | 10/1995 |
| JP | 8-66883 A | 3/1996 |
| JP | 08-215204 A | 8/1996 |
| JP | 08-243080 A | 9/1996 |
| JP | 10-128538 A | 5/1998 |
| JP | 11-300662 A | 11/1999 |
| JP | 2000-312684 A | 11/2000 |
| JP | 2001-087281 A | 4/2001 |
| JP | 2001-113481 A | 4/2001 |
| JP | 2001-277157 A | 10/2001 |
| JP | 2001-309920 A | 11/2001 |
| JP | 2002-014287 A | 1/2002 |
| JP | 2002-059380 A | 2/2002 |
| JP | 2002-102248 A | 4/2002 |
| JP | 2002-272758 A | 9/2002 |
| JP | 2002-537884 A | 11/2002 |
| JP | 2003-024336 A | 1/2003 |
| JP | 2003-053685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-312991 A | 11/2005 |
| JP | 2006-061272 A | 3/2006 |
| JP | 2006-167867 A | 6/2006 |
| JP | 2006-288955 A | 10/2006 |
| JP | 2006-321027 A | 11/2006 |
| JP | 2007-029274 A | 2/2007 |
| JP | 2007-038315 A | 2/2007 |
| JP | 2007-98507 A | 4/2007 |
| JP | 2007-105485 A | 4/2007 |
| JP | 3999816 B2 | 10/2007 |
| JP | 2008-000282 A | 1/2008 |
| JP | 2008-036793 A | 2/2008 |
| JP | 4058113 B2 | 3/2008 |
| JP | 2008-93270 A | 4/2008 |
| JP | 2008-173724 A | 7/2008 |
| JP | 4129313 B2 | 8/2008 |
| JP | 4176126 B2 | 11/2008 |
| JP | 2009-028157 A | 2/2009 |
| JP | 2009-056164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226093 A | 10/2009 |
| JP | 2009-269127 A | 11/2009 |
| JP | 2010-504127 A | 2/2010 |

(56) References Cited

FOREIGN PATENT DOCUMENTS

| | | | |
|---|---|---|---|
| JP | 2010-076012 | A | 4/2010 |
| JP | 2010-524548 | A | 7/2010 |
| JP | 2011-509112 | A | 3/2011 |
| JP | 2011-206213 | A | 10/2011 |
| JP | 2012-091310 | A | 5/2012 |
| WO | 97/16123 | A1 | 5/1997 |
| WO | 97/16124 | A1 | 5/1997 |
| WO | 97/29690 | A1 | 8/1997 |
| WO | 98/25666 | A1 | 6/1998 |
| WO | 00/51486 | A1 | 9/2000 |
| WO | 00/60421 | A2 | 10/2000 |
| WO | 03/049596 | A2 | 6/2003 |
| WO | 2006/111966 | A2 | 10/2006 |
| WO | 2007/047782 | A2 | 4/2007 |
| WO | 2007/075864 | A1 | 7/2007 |
| WO | 2007/111955 | A2 | 10/2007 |
| WO | 2007/126443 | A2 | 11/2007 |
| WO | 2007/138674 | A1 | 12/2007 |
| WO | 2008/038184 | A2 | 4/2008 |
| WO | 2008/108289 | A1 | 9/2008 |
| WO | 2009/034477 | A2 | 3/2009 |
| WO | 2009/089614 | A1 | 7/2009 |
| WO | 2010/006057 | A1 | 1/2010 |
| WO | 2010/109932 | A1 | 9/2010 |
| WO | 2011/025786 | A1 | 3/2011 |
| WO | 2011/060139 | A2 | 5/2011 |
| WO | 2011/060185 | A1 | 5/2011 |
| WO | 2011/085815 | A1 | 7/2011 |
| WO | 2012/042949 | A1 | 4/2012 |

OTHER PUBLICATIONS

International Search Report dated Oct. 23, 2012 issued in PCT/JP2012/070414.
International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.
International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
U.S. Office Action dated Apr. 9, 2015 received in related U.S. Patent Application, namely U.S. Appl. No. 14/169,675.
U.S. Office Action dated May 8, 2015 received in related U.S. Patent Application, namely U.S. Appl. No. 14/157,920.
Notice of Allowance dated Jan. 20, 2015 from related U.S. Appl. No. 13/566,023.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0666.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Extended Supplementary European Search Report dated Mar. 27, 2015 from related European Application No. 12 82 0056.5.
Chinese Office Action dated Jun. 3, 2015 from related Chinese Application No. 201280035926.3, together with an English language translation.
Chinese Office Action dated Jul. 1, 2015 from related Chinese Application No. 201280037244.6, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.
Office Action dated Sep. 16, 2015 received in related U.S. Appl. No. 13/566,012.
Office Action dated Nov. 19, 2015 received in related U.S. Appl. No. 14/157,920.

* cited by examiner

FIG. 5A1
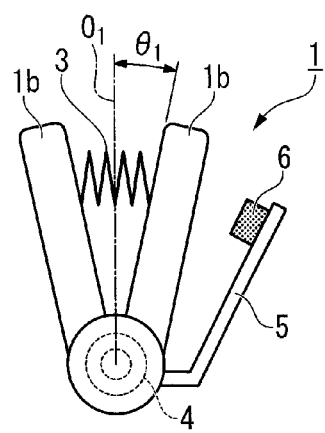
FIG. 5A2
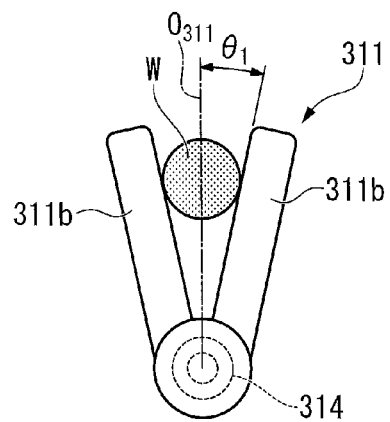
FIG. 5B1
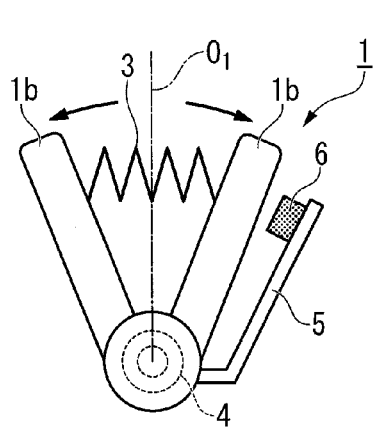
FIG. 5B2
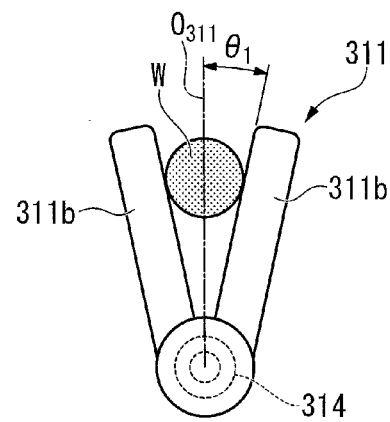
FIG. 5C1
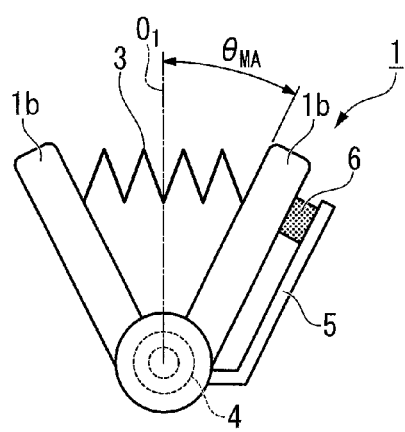
FIG. 5C2
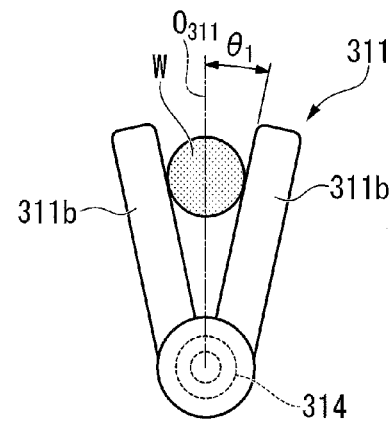

FIG. 6A1 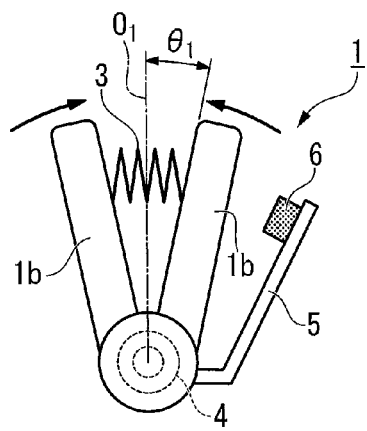
FIG. 6A2 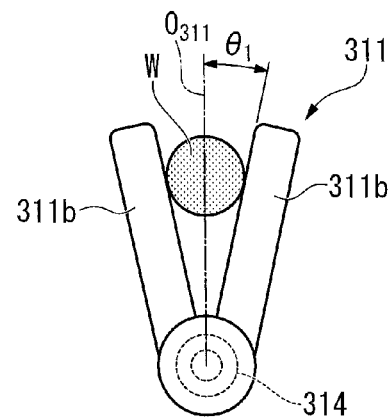
FIG. 6B1 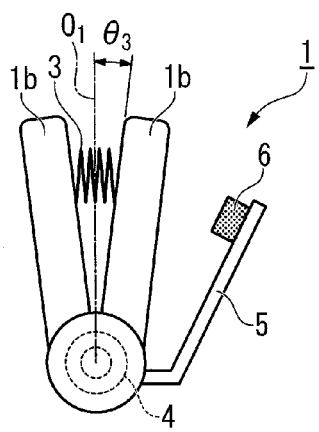
FIG. 6B2 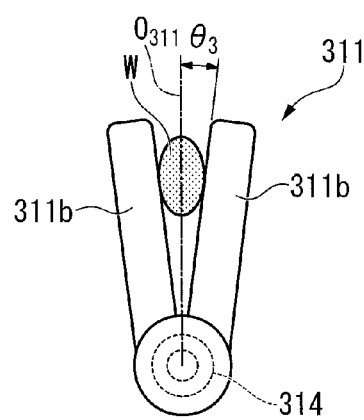
FIG. 6C1 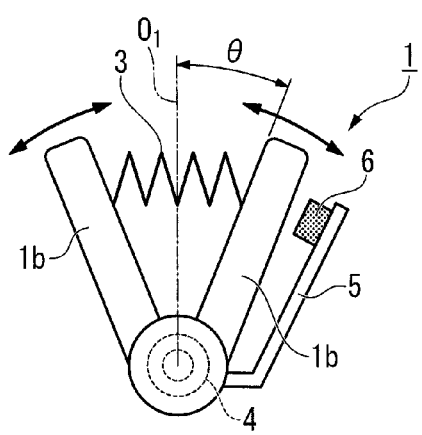
FIG. 6C2 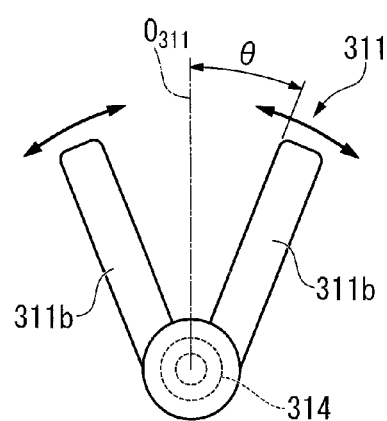

MANIPULATOR SYSTEM

This application is a continuation application based on a PCT Patent Application No. PCT/JP2012/070417, filed on Aug. 3, 2012, whose priority is claimed on Japanese Patent Application No. 2012-116740, filed on May 22, 2012, and U.S. Provisional Patent Application No. 61/515,203, filed Aug. 4, 2011. The contents of all of the PCT Application, the Japanese Application, and the U.S. Provisional Patent Application are incorporated herein by reference.

TECHNICAL FIELD

The present invention relates to a manipulator system, and more particularly, to a master-slave type medical manipulator system.

BACKGROUND ART

In the past, master-slave type manipulator systems have been known as medical manipulators that support surgical operations. The medical manipulators according to the related art include a master grip (master manipulation unit) that manipulates and inputs an operation of a tool (slave motion unit) mounted on a slave manipulator and used for a surgical operation. In a medical manipulator, a movement of a master grip is transmitted to a tool when a surgeon who is an operator manipulates the master grip. Forceps, needle holders, and the like are used as the tools to which a movement of the master grip is transmitted.

For example, as a manipulator system according to the related art, a medical robot system is disclosed in U.S. Pat. No. 7,778,733. In the medical robot system, opening and closing operations of an end effector are controlled by opening and closing an input handle.

SUMMARY OF THE INVENTION

According to a first aspect of the present invention, a manipulator system includes a master manipulation unit, a slave motion unit, an interlock control unit, and an interlock permission input unit. An operator performs a manipulation input using the master manipulation unit. The slave motion unit is configured to operate in accordance with the manipulation input. The interlock control unit analyzes the manipulation input and performs control to operate the slave motion unit, interlocking with the manipulation input. The interlock permission input unit is able to be manipulated by the operator and transmits, to the interlock control unit, an interlock permission mode signal used to enter a mode in which interlock of the slave motion unit is permitted based on the manipulation input of the mater manipulation unit when the operator manipulates the interlock permission input unit. The interlock control unit stops the interlock control when the operation of the slave motion unit is deviated from an operation corresponding to the manipulation input, and monitors the manipulation input of the master manipulation unit and an operation state of the slave motion unit. The interlock control unit interlocks the operation of the slave motion unit with the operation corresponding to the manipulation input after the interlock control unit receives the interlock permission mode signal, when detects that the manipulation input matches the operation state.

According to a second aspect of the present invention, in the manipulator system according to the first aspect of the present invention, the master manipulation unit of the manipulator system may include a manipulation member and a master angle detection unit. The manipulation member may be provided to be opened and closed in order to perform the manipulation input. The master angle detection unit may detect an opening and closing angle of the manipulation member and transmits a detection value of the opening and closing angle of the manipulation member to the interlock control unit. The slave motion unit may include an opening and closing motion unit and a slave angle detection unit. The opening and closing motion unit may be provided to be opened and closed. The slave angle detection unit may detect an opening and closing angle of the opening and closing motion unit and transmits a detection value of the opening and closing angle of the opening and closing motion unit to the interlock control unit. The interlock control unit may interlock the slave motion unit with an operation corresponding to the manipulation input after the interlock control unit receives the interlock permission mode signal, when the detection value of the opening and closing angle of the manipulation member corresponds to the detection value of the opening and closing angle of the opening and closing motion unit, as well as when the detection value of the opening and closing angle of the manipulation member is changed in a closing direction of the manipulation member.

According to a third aspect of the present invention, the manipulation system according to the first or second aspect of the present invention may include an information display unit. The information display unit may display information transmitted from the interlock control unit. The interlock control unit may display restart of interlock on the information display unit after the interlock control unit receives the interlock permission mode signal, when the interlock control unit detects that the slave motion unit may interlock with the operation corresponding to the manipulation input.

According to a fourth aspect of the present invention, in the manipulation system according to the second or third aspect, the interlock permission input unit may be configured by a position detection switch that detects that the manipulation member is moved to a maximum opening position and generates the interlock permission mode signal.

According to a fifth aspect of the present invention, in the manipulation system according to the second or third aspect, the interlock permission input unit may be configured by an input switch provided on a surface of the master manipulation unit.

According to a sixth aspect of the present invention, in the manipulation system according to the second or third aspect, the interlock permission input unit may be configured by an input switch that is provided separately from the master manipulation unit.

According to a seventh aspect of the present invention, in the manipulation system according to the sixth aspect, the input switch may be configured by a footswitch.

According to an eighth aspect of the present invention, in the manipulation system according to any one of the first to seventh aspects, the master manipulation unit may include a manipulation member and a master angle detection unit. The manipulation member may be provided to be opened and closed in order to perform the manipulation input. The master angle detection unit may detect an opening and closing angle of the manipulation member and transmit a detection value of the opening and closing angle of the manipulation member to the interlock control unit. The slave motion unit may include an opening and closing motion unit and a slave angle detection unit. The opening and closing motion unit may be provided to be opened and closed. The slave angle detection unit may detect an opening and closing angle of the opening and closing motion unit and may transmit a detection value of the opening and closing angle of the opening and closing motion unit to the interlock control unit. The interlock control unit may interlock the slave motion unit with an operation corresponding to the manipulation input after the interlock control unit receives the interlock permission mode signal, when the detection value of the opening and closing angle of the manipulation member corresponds to the detection value of the opening and closing angle of the opening and closing motion unit, as well as when the detection value of the opening and closing angle of the manipulation member is changed in an opening direction of the manipulation member.

According to a ninth aspect of the present invention, in the manipulation system according to any one of the first to seventh aspects, the master manipulation unit may include a manipulation member and a master angle detection unit. The manipulation member may be provided to be opened and closed in order to perform the manipulation input. The master angle detection unit may detect an opening and closing angle of the manipulation member and transmit a detection value of the opening and closing angle of the manipulation member to the interlock control unit. The slave motion unit may include an opening and closing motion unit and a slave angle detection unit. The opening and closing motion unit may be provided to be opened and closed. The slave angle detection unit may detect an opening and closing angle of the opening and closing motion unit and transmit a detection value of the opening and closing angle of the opening and closing motion unit to the interlock control unit. The interlock control unit may be configured to interlock the slave motion unit with an operation corresponding to the manipulation input after the interlock control unit receives the interlock permission mode signal, when the detection value of the opening and closing angle of the manipulation member corresponds to the detection value of the opening and closing angle of the opening and closing motion unit, as well as when the detection value of the opening and closing angle of the manipulation member is changed in an opening or closing direction of the manipulation member. The interlock control unit may be configured to select the interlock of the case in which the detection value is changed in the opening direction or the interlock of the case in which the detection value is changed in the closing direction.

BRIEF DESCRIPTION OF THE DRAWINGS

FIG. 5A1 is a diagram illustrating the operation of the manipulator system according to the embodiment of the present invention.

FIG. 5A2 is a diagram illustrating the operation of the manipulator system according to the embodiment of the present invention.

FIG. 5B1 is a diagram illustrating the operation of the manipulator system according to the embodiment of the present invention.

FIG. 5B2 is a diagram illustrating the operation of the manipulator system according to the embodiment of the present invention.

FIG. 5C1 is a diagram illustrating the operation of the manipulator system according to the embodiment of the present invention.

FIG. 5C2 is a diagram illustrating the operation of the manipulator system according to the embodiment of the present invention.

FIG. 6A1 is a diagram illustrating the operation of the manipulator system continued from FIGS. 5A1 to 5C2 according to the embodiment of the present invention.

FIG. 6A2 is a diagram illustrating the operation of the manipulator system continued from FIGS. 5A1 to 5C2 according to the embodiment of the present invention.

FIG. 6B1 is a diagram illustrating the operation of the manipulator system continued from FIGS. 5A1 to 5C2 according to the embodiment of the present invention.

FIG. 6B2 is a diagram illustrating the operation of the manipulator system continued from FIGS. 5A1 to 5C2 according to the embodiment of the present invention.

FIG. 6C1 is a diagram illustrating the operation of the manipulator system continued from FIGS. 5A1 to 5C2 according to the embodiment of the present invention.

FIG. 6C2 is a diagram illustrating the operation of the manipulator system continued from FIGS. 5A1 to 5C2 according to the embodiment of the present invention.

DESCRIPTION OF EMBODIMENTS

Hereinafter, an embodiment of the present invention will be described with reference to the drawings.

First, a manipulator system according to the embodiment will be described.

Figure 1:
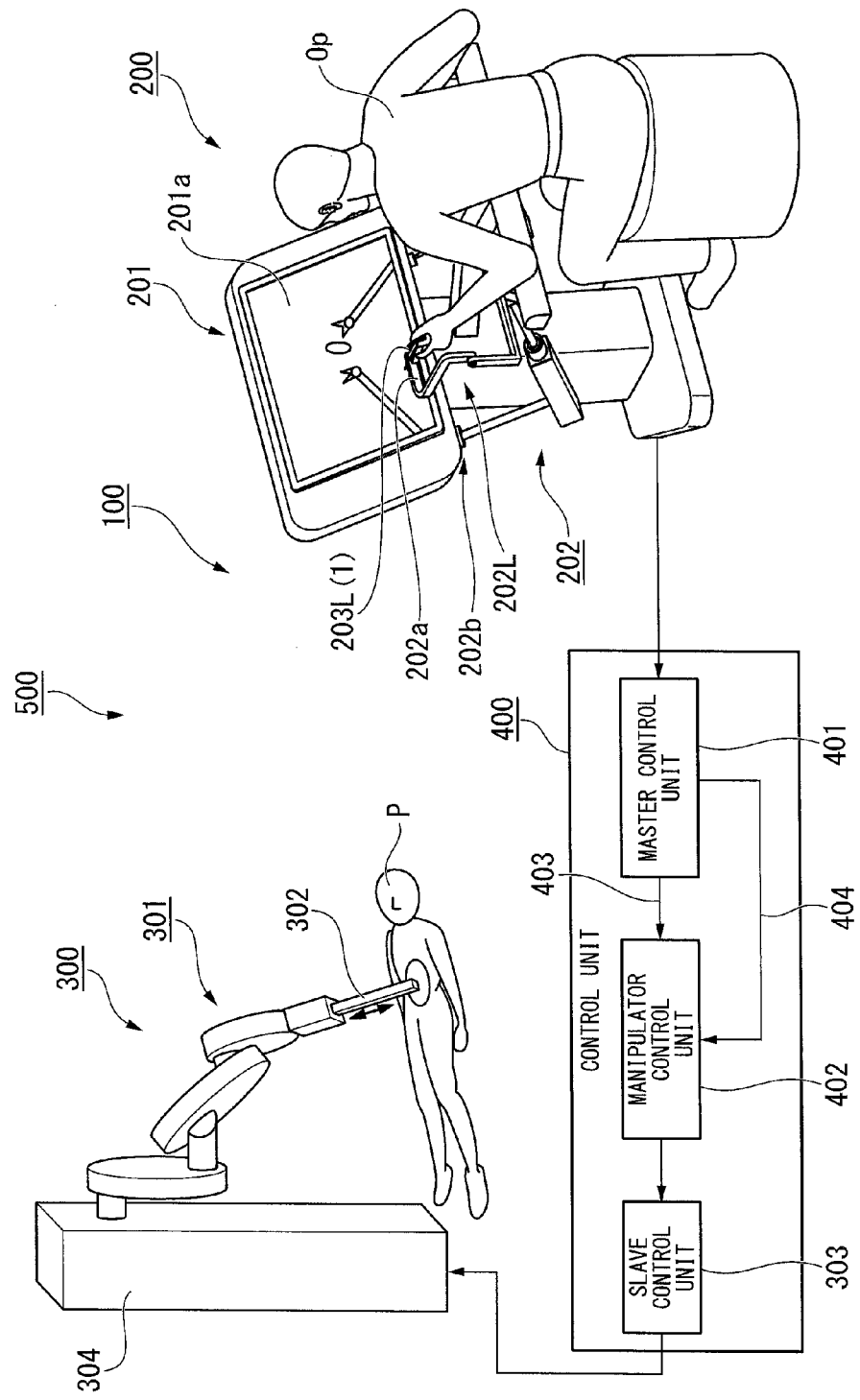
FIG. 1 is a schematic perspective view illustrating the overall configuration of a manipulator system according to an embodiment of the present invention.
Figure 2:
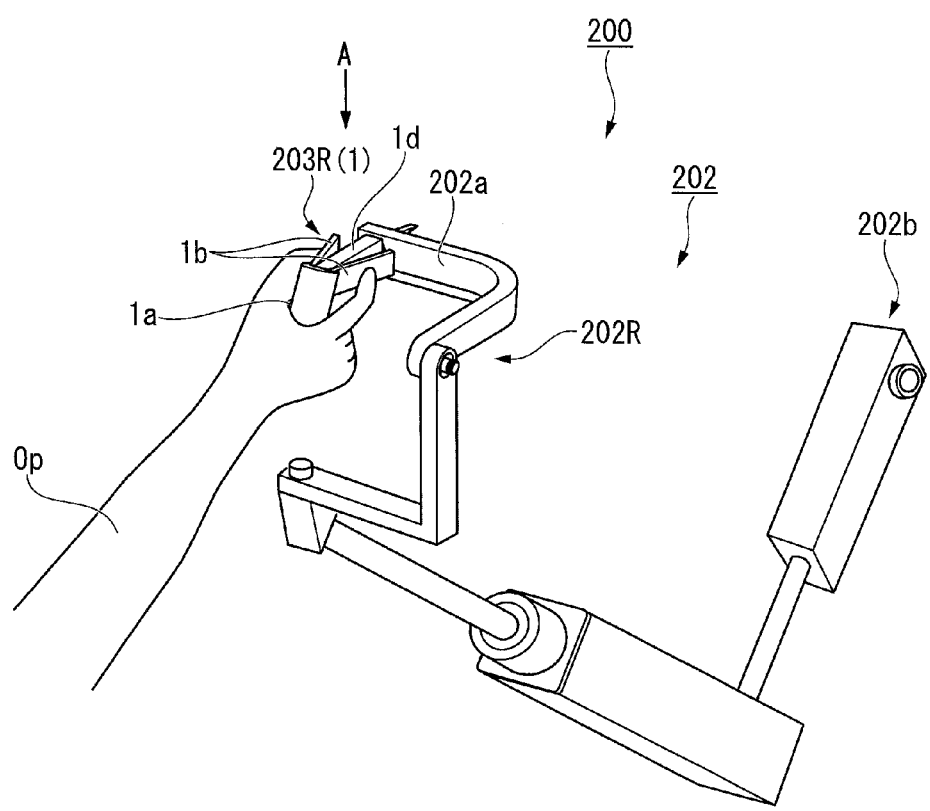
FIG. 2 is a schematic perspective view illustrating another master manipulation unit included in the manipulator system in FIG. 1.
Figure 3:
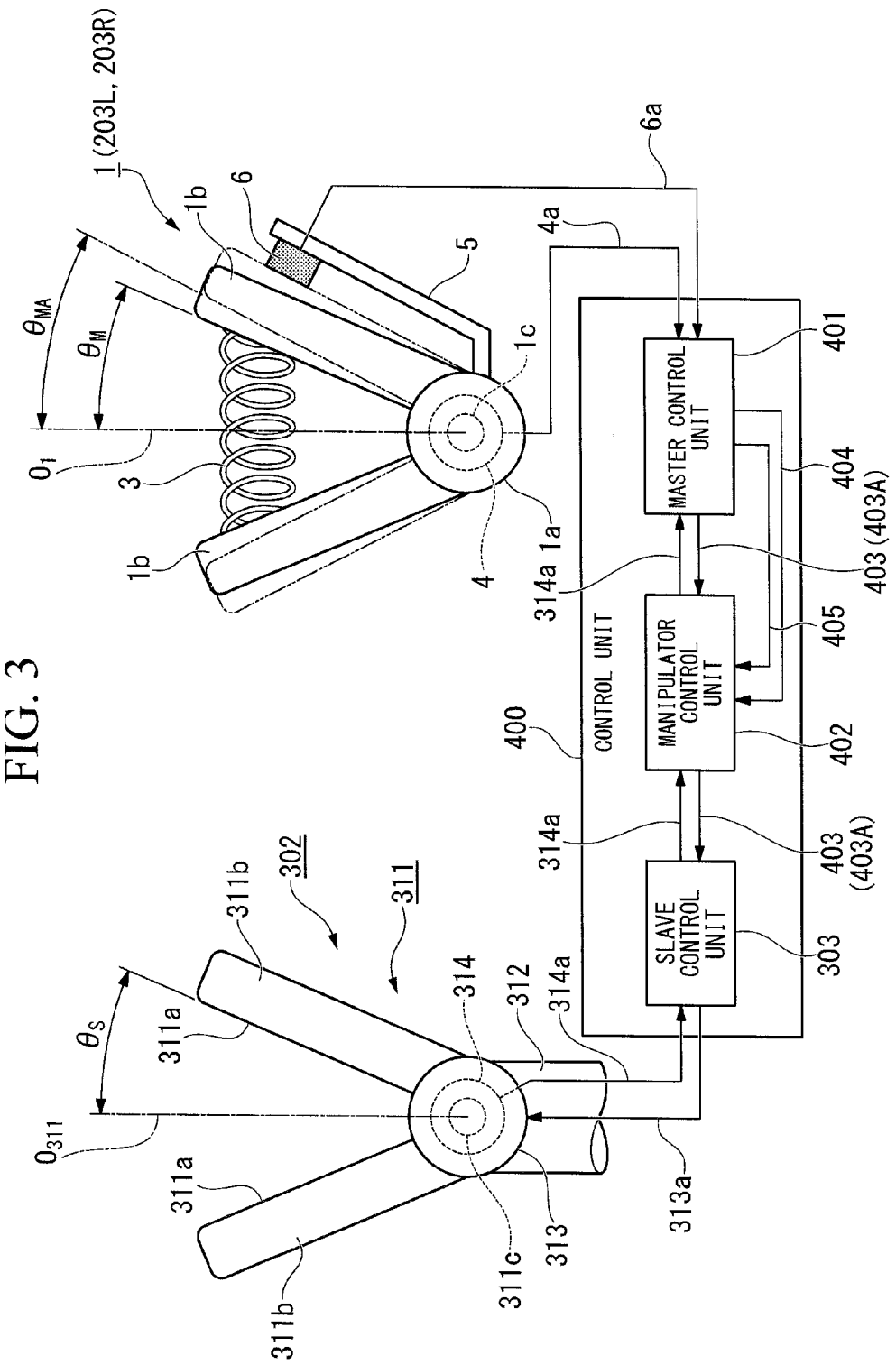
FIG. 3 is a schematic system configuration diagram illustrating a system configuration of main units of the manipulator system according to the embodiment of the present invention.

FIG. 1 is a schematic perspective view illustrating the overall configuration of the manipulator system according to this embodiment. FIG. 2 is a schematic perspective view illustrating another master manipulation unit included in the manipulator system in FIG. 1. FIG. 3 is a schematic diagram illustrating the configuration of main units of the manipulator system according to the embodiment of the present invention.

As shown in FIG. 1 (some portions are shown in FIGS. 2 and 3), a master-slave manipulator 500 (manipulator system) according to this embodiment is, for example, a medical manipulator that is used to perform a surgical operation. The master-slave manipulator 500 includes a slave manipulator 300 and a manipulation input device 100. The manipulation input device 100 receives a manipulation input from an operator Op and remotely manipulates an operation of the slave manipulator 300.

The slave manipulator 300 includes a treatment tool 302, a slave arm 301, a slave control unit 303, and a holding body 304. The slave arm 301 movably holds the treatment tool 302 in periphery of a patient P. The slave control unit 303 controls operations of movable units of the treatment 302 and the slave arm 301. The holding body 304 holds the treatment tool 302 and the slave arm 301.

In FIG. 1, which is a schematic diagram, for example, the single treatment tool 302 and the single slave arm 301 are installed. However, a plurality of treatment tools 302 and a plurality of slave arms 301 may be installed. When the plurality of treatment tools 302 and the plurality of slave arms 301 are installed, the operator Op can select two thereof and simultaneously manipulate the two with right and left hands of the operator Op.

Some of the signals in the functional block diagram are not illustrated.

Various surgical instruments or treatment tools used for surgical operations may be used as the treatment tool 302. Hereinafter, for example, the treatment tool 302 including an opening and closing unit 311 (a slave motion unit or an opening and closing motion unit) and an opening and closing driving unit 313 as in FIG. 3 will be described. The opening and closing unit 311 is installed at the distal end (which is an end facing a body cavity of the patient P) of a shaft-like unit 312 and performs opening and closing operations. The opening and closing driving unit 313 opens and closes the opening and closing unit 311.

Examples of the treatment tool 302 include forceps and needle holders.

The opening and closing unit 311 includes a pair of treatment tool pieces 311b. The pair of treatment tool pieces 311b performs opening and closing about a rotation shaft 311c in a bilaterally symmetrical manner with respect to an opening and closing central axial line $O_{311}$.

In FIG. 3, the opening and closing central axial line $O_{311}$ aligns with the central axial line of the shaft-like unit 312. However, the opening and closing unit 311 may be connected to the shaft-like unit 312 via a joint (not shown). In this case, the opening and closing central axial line $O_{311}$ may be inclined with respect to the central axial line of the shaft-like unit 312.

Hereinafter, an angle $\theta_S$ is used as an opening and closing angle of the opening and closing unit 311. The angle $\theta_S$ is an angle formed by the opening and closing central axial line $O_{311}$ and a gripping surface 311a of the treatment tool piece 311b. That is, the angle $\theta_S$ is half of the angle formed by each gripping surface 311a.

Therefore, when the treatment tool piece 311b is moved in an opening direction, the angle $\theta_S$ increases. When the treatment tool piece 311b is moved in a closing direction, the angle $\theta_S$ decreases.

However, this definition of the opening and closing angle is merely an example. For another example, an angle $2\theta_S$ which is an angle formed by the gripping surfaces 311a may be used.

An operation of the opening and closing driving unit 313 is controlled by a driving signal 313a that is transmitted from the slave control unit 303 based on a driving command value 403 transmitted from a control unit 400. Therefore, the opening and closing driving unit 313 is electrically connected to the control unit 400 via the slave control unit 303 to be described below.

The opening and closing driving unit 313 can be configured appropriately using an actuator that opens and closes the opening and closing unit 311.

The opening and closing driving unit 313 includes an encoder 314 (slave angle detection unit) that detects the opening and closing angle of the opening and closing driving unit 313.

The encoder 314 is configured to generate an output signal 314a corresponding to the detected opening and closing angle and transmit the generated output signal 314a to the slave control unit 303.

The configuration of the encoder 314 is not particularly limited. For example, a rotary encoder that directly detects the amount of rotation of the opening and closing unit 311 may be used. The encoder 314 may be configured as a linear encoder that detects the amount of movement of a linear movement member, which interlocks with opening and closing operations of the opening and closing unit 311, or may be configured as a rotary encoder that detects an amount of movement by converting an amount of linear movement into an amount of rotary movement.

The encoder 314 may be an absolute type encoder or an increment type encoder.

When the increment type encoder is used, an appropriate position correction means is provided. The position correction means monitors whether the treatment tool piece 311b reaches a given correction position. In the case of the increment type encoder, the output signal 314a of the encoder 314 is preferably reset when the treatment tool piece 311b reaches the correction position. In this configuration, the output signal 314a can be corrected whenever the treatment tool piece 311b passes through the correction position. Therefore, even the increment type encoder can accurately detect the opening and closing angle of the opening and closing unit 311.

The slave arm 301 is configured as a multi joint arm that holds the treatment tool 302 at an appropriate position and an appropriate orientation. The slave arm 301 is electrically connected to the slave control unit 303, and thus an operation of the slave arm 301 is controlled by a control signal from the slave control unit 303.

As shown in FIG. 1, the slave control unit 303 controls the slave manipulator 300 based on a control signal from a manipulator control unit 402 to be described below. The slave control unit 303 transmits information on the position of each movable unit transmitted from the slave manipulator 300, a detection signal necessary for control, or the like to the manipulator control unit 402. Therefore, the slave control unit 303 is electrically connected to the manipulator control unit 402 of the control unit 400 to be described below and each movable unit of the slave manipulator 300.

For example, the slave control unit 303 transmits the driving signal 313a used to open or close the opening and closing unit 311 to the opening and closing unit 311 of the treatment tool 302 based on the driving command value 403 and controls the opening and closing operations.

The slave control unit 303 acquires the output signal 314a from the encoder 314 and transmits the acquired output signal 314a to the manipulator control unit 402.

As shown in FIG. 1, the manipulation input device 100 includes a master input section 200 and the control unit 400 (interlock control unit).

The master input section 200 functions as a master that delivers an operation from the operator Op to the slave manipulator 300. The master input section 200 includes a display unit 201 (information display unit), a master arm 202, and master grips 203L and 203R (master manipulation unit).

The display unit 201 is electrically connected to a camera (not shown) and the control unit 400. The display unit 201 displays information from the camera or the control unit 400 so that the operator Op can view the information.

Examples of kinds of information displayed by the display unit 201 include a video of surgical parts and the vicinity of the surgical parts of the patient P photographed by the camera, a manipulation input screen regarding a manipulation input performed by input means (not shown) such as a footswitch, various kinds of information on the operator Op, guidance, and characters or images of warning messages.

The master arm 202 delivers, to the slave manipulator 300, manipulation performed to manipulate the position and orientation of the slave arm 301 of the slave manipulator 300 by the operator Op. The master arm 202 is connected to communicate with the control unit 400.

For example, the master arm 202 according to this embodiment includes two multi joint arms, that is, a multi joint arm 202L (see FIG. 1) and a multi joint arm 202R (see FIG. 2.) of which an arm proximal end 202b is connected to a fixed position of a lower unit of the display unit 201 inside the master input section 200.

The multi joint arms 202L and 202R are disposed on the front side of the display unit 201 so that the operator Op can perform manipulation while viewing the display unit 201.

The multi joint arms 202L and 202R correspond to manipulation inputs performed with the left and right hands of the operator Op, respectively.

Master grips 203L and 203R gripped to perform a manipulation input by the operator Op are installed in the arm distal end 202a of the multi joint arms 202L and 202R on the side of the operator Op.

The multi joint arms 202L and 202R each include an encoder that detects an amount of operation of a joint for each joint and transmit the output of each encoder as a manipulation signal of each joint to the control unit 400.

The operator Op manipulates the master grips 203L and 203R with his or her left and right hands to perform a manipulation input on the slave arm 301 corresponding to the multi joint arms 202L and 202R and the treatment tool 302 installed in the slave arm 301.

The master grips 203L and 203R can be provided in a bilaterally symmetrical shape so that the operator Op can easily grip or manipulate the master grips 203L and 203R with his or her left and right hands. Hereinafter, the master grips 203L and 203R configured as master grips 1 (see FIG. 3) with the same shape will be described.

As shown in the schematic diagram of FIG. 3, the master grip 1 includes a grip unit 1a, a casing unit 1d, manipulation handles 1b (manipulation member), a spring 3, an encoder 4 (master angle detection unit), and a position detection switch 6 (interlock permission input unit).

FIG. 3 is a plan view when viewed from A of FIG. 2. However, since the master grip 1 is schematically illustrated in FIG. 3, for example, the casing unit 1d shown in FIG. 2 is not illustrated.

The grip unit 1a has a cylindrical shape gripped by one hand of the operator Op, as shown in FIG. 2. The grip unit 1a includes the casing unit 1d extending toward the arm distal end 202a at one end thereof.

The distal end of the casing unit 1d is connected to the arm distal end 202a.

At the end of the grip unit 1a, a pair of manipulation handles 1b are movably held with the casing unit 1d interposed therebetween. In the grip unit 1a, the manipulation handles 1b are opened in a V shape so that the opening and closing angle can be changed.

In this embodiment, as shown in FIG. 3, the end of each manipulation handle 1b is rotatably held by a rotation shaft 1c installed inside the grip unit 1a.

Each manipulation handle 1b has an appropriate shape such as a bar shape or a plate shape, as long as the fingers of the operator Op can lock with the manipulation handle 1b to perform opening and closing operations. For example, a concavo-convex unit may be formed so that a gripping position for the operator Op can be identified. Although not illustrated, the manipulation handle 1b may be configured to easily follow a movement of the fingers of the operator Op. For example, protrusion units with which the fingers performing manipulation lock in the opening and closing directions or finger insertion units in which the fingers are inserted may be formed.

The spring 3 is a spring member that biases the pair of manipulation handles 1b in the opening direction. The spring 3 is mounted between the manipulation handles 1b at a position on the side of the distal end (the end opposite to the gripping unit 1a) of the manipulation handles 1b.

However, neither a kind of spring 3 nor the mounting position of the spring 3 mounted between the manipulation handles 1b is particularly limited, as long as the manipulation handles 1b are biased in the opening direction. In FIG. 3, for example, both ends of a helical compression spring are mounted on the side surfaces of the manipulation handles 1b facing each other.

The length of the spring 3 is set to a constant value determined so that the opening and closing angle of the manipulation handles 1b is smaller than the maximum opening and closing angle when manipulation is not performed.

In this configuration, when no outside force is applied to the manipulation handles 1b (hereinafter, this state is referred to as a natural state), the master grip 1 is configured to be opened in the V shape at the constant opening and closing angle by the biasing force of the spring 3, as indicated by a solid line in FIG. 3.

When the operator Op grips the grip unit 1a with his or her hand, for example, when the operator Op grips the manipulation handles 1b with his or her thumb and forefinger and moves the manipulation handles 1b, the manipulation handles 1b are rotated about the rotation shaft 1c and the opening and closing angle is thus changed.

Hereinafter, an angle $\theta_M$ is used as the opening and closing angle of the manipulation handles 1b of the master grip 1. The angle $\theta_m$ is an angle that is formed by the opening and closing central axial line $O_1$ and the manipulation handle 1b. That is, the angle $\theta_M$ is half of the angle formed by the manipulation handles 1b.

However, this definition of the opening and closing angle is merely an example. For example, an angle $2\theta_S$ which is an angle formed by the manipulation surfaces 311a may be used as the opening and closing angle.

Thus, when the manipulation handles 1b are opened or closed, the reactive force from the spring 3 is generated in accordance with the expansion or contraction degree of the spring 3. Therefore, the operator Op feels a manipulation resistance. For example, when the manipulation handles 1b are gradually closed, the manipulation resistance increases with a decrease in the opening and closing angle. Therefore, when the operator Op manipulates the pair of manipulation handles 1b, the operator Op can have the sense of gripping an actual grip object.

In this embodiment, the operator Op can manipulate the manipulation handles 1b to further open the manipulation handles 1b from the natural state. Hereinafter, the angle $\theta_{MA}$ is referred to as the maximum opening and closing angle.

In the manipulation performed to further open the manipulation handles 1b from the natural state, the manipulation resistance is generated due to an elastic restoring force of the tension of the spring 3. The manipulation resistance increases, as the opening and closing angle approaches the maximum opening and closing angle.

The encoder 4 detects the opening and closing angle of the manipulation handles 1b and transmits a detection value corresponding to the opening and closing angle as an output signal 4a to the control unit 400. In this embodiment, the encoder 4 is provided inside the grip unit 1a and is electrically connected to the control unit 400.

In this embodiment, a rotary encoder that directly detects an amount of rotation of the manipulation handles 1b is used as the encoder 4. However, the encoder 4 may be configured as a linear encoder that detects the amount of movement of a linear movement member, which interlocks with opening and closing operations of the manipulation handles 1b, or may be configured as a rotary encoder that detects an amount of movement by converting an amount of linear movement into an amount of rotary movement.

The encoder 4 may be an absolute type encoder or an increment type encoder.

When the increment type encoder is used, appropriate position correction means is provided. The position correction means monitors whether the manipulation handles 1b reach given correction positions. In the case of the increment type encoder, the output signal 4a of the encoder 4 is preferably reset when the manipulation handles 1b reach the correction position. In this configuration, the output signal 4a can be corrected whenever the manipulation handles 1b pass through the correction position. Therefore, even the increment type encoder can accurately detect the opening and closing angle of the manipulation handles 1b.

The position detection switch 6 is a position detector that detects that the manipulation handles 1b are opened up to the maximum opening and closing angle by detecting the position of one of the manipulation handles 1b, generates an interlock permission mode signal 6a, and transmits the interlock permission mode signal 6a to the control unit 400. The position detection switch 6 is electrically connected to the control unit 400.

The interlock permission mode signal 6a is used to enter a mode (hereinafter referred to as an interlock permission mode) in which the control unit 400 permits the interlock of the opening and closing unit 311 based on a manipulation input of the master grip 1.

Examples of the kinds of position detection switch 6 include a contact switch detecting that an object mechanically comes into contact with the manipulation handles 1b, a position detection sensor that electrically, magnetically, or optically detects the movement positions of the manipulation handles 1b, and a speed detection sensor.

In this embodiment, the position detection switch 6 is mounted on a holding arm member 5, of which an end is fixed to the grip unit 1a, to face one of the manipulation handles 1b in the opening direction when the manipulation handles 1b are opened to the maximum angle.

The holding arm member 5 extends from the grip unit 1a so that the holding arm member 5 faces one of the manipulation handles 1b opened by the maximum angle, as indicated by a two-dot chain line in FIG. 3, on the opposite side to the opening and closing central axial line $O_1$.

The control unit 400 includes a master control unit 401 and the manipulator control unit 402, as shown in FIG. 1, as the functional configuration.

The master control unit 401 receives a signal transmitted from the master input section 200 and analyzes an amount of driving of a movable unit to be controlled by the slave manipulator 300 to perform an operation based on the signal. The master control unit 401 transmits a movable unit selection signal 404 and a driving command value 403 for a movable unit selected by the movable unit selection signal 404 to the manipulator control unit 402.

Here, the movable unit selection signal 404 is independently allocated to each movable unit such as a joint of the slave arm 301 and the opening and closing unit 311 of the treatment tool 302 held by the slave arm 301.

The master control unit 401 analyzes a signal from each joint of the master arm 202 and calculates the positions and orientations of the master grips 203L and 203R. As a result, the master control unit 401 can generate the driving command value 403 of each movable unit of the slave arm 301 necessary to control the position and orientation of the distal end of the treatment tool 302 held by the slave arm 301. The driving command value 403 is transmitted to the slave control unit 303 together with the movable unit selection signal 404 corresponding to each movable unit.

The master control unit 401 can also generate the driving command value 403 to be transmitted to the opening and closing unit 311 based on the output signal 4a from the encoders 4 corresponding to the master grips 203L and 203R to the master control unit 401, and then can transmit the generated driving command value 403 to the manipulator control unit 402. The driving command value 403 is specifically referred to as an opening and closing command value 403A.

A correspondence relation between the output signal 4a and the opening and closing command value 403A is stored as, for example, a table or conversion expression data in a storage unit (not shown) of the master control unit 401. The correspondence relation can be set as necessary.

For example, the correspondence relation in which the opening and closing angle $\theta_M$ of the manipulation handles 1b coincides with the opening and closing angle $\theta_S$ of the opening and closing unit 311 may be established. The correspondence relation between the opening and closing angle $\theta_M$ and the opening and closing angle $\theta_S$ may be linear at an appropriate ratio. The correspondence relation between the opening and closing angle $\theta_M$ and the opening and closing angle $\theta_S$ may not be linear.

The master control unit 401 is configured to selectively switch between an "interlock mode" and an "interlock stop mode" by transmitting the control signal 405 to the manipulator control unit 402.

Here, the "interlock mode" is a mode in which the opening and closing command value 403A is transmitted to the slave control unit 303 by performing communication between the manipulator control unit 402 and the slave control unit 303 and an operation of the opening and closing unit 311 is interlocked with an operation based on the opening and closing command value 403A.

Further, the "interlock stop mode" is a mode in which the transmission of the opening and closing command value 403A to the slave control unit 303 is stopped by stopping the communication between the manipulator control unit 402 and the slave control unit 303, and thus the interlock operation based on the opening and closing command value 403A is stopped.

However, in the interlock stop mode, the output signal 314a continues to be transmitted from the encoder 314. The output signal 314a continues to be transmitted to the master control unit 401 via the slave control unit 303 and the manipulator control unit 402.

The interlock mode starts after the master control unit 401 receives the interlock permission mode signal 6a, and when the opening and closing angle of the manipulation handles 1b detected by the output signal 4a corresponds to the opening and closing angle of the opening and closing unit 311 detected by the output signal 314a, also when the opening and closing angle of the manipulation handles 1b detected by the output signal 4a is changed in the closing direction of the manipulation handles 1b.

Here, the "correspondence" between the opening and closing angle of the manipulation handles 1b and the opening and closing angle of the opening and closing unit 311 means that the opening and closing angle indicated by the opening and closing command value 403A generated from the output signal 4a coincides with the opening and closing angle of the opening and closing unit 311 detected by the output signal 314a based on the preset correspondence. That is, when the correspondence relation is expressed by a function f, a relation of "$\theta_S = f(\theta_M)$" is satisfied.

When such a correspondence relation is satisfied, the manipulation input of the manipulation handles 1b matches the operation state of the opening and closing unit 311 based on the correspondence relation.

In the interlock stop mode, the master control unit 401 starts transmitting the control signal 405 to the manipulator control unit 402 when an operation of the opening and closing unit 311 is deviated from the operation based on the opening and closing command value 403A by a value equal to or greater than an allowance value.

Therefore, the master control unit 401 acquires the output signal 314a transmitted from the encoder 314 via the slave control unit 303 and the manipulator control unit 402 and monitors whether the opening and closing unit 311 interlocks in accordance with the opening and closing command value 403A.

The manipulator control unit 402 communicates with each movable unit of the slave manipulator 300 selected by the movable unit selection signal 404 via the slave control unit 303 and controls an operation of each movable unit in order to execute the operation based on the driving command value 403 transmitted from the master control unit 401.

In particular, the manipulator control unit 402 transmits the opening and closing command value 403A to the slave control unit 303 until the mode is switched to the interlock stop mode by the control signal 405. Thus, the slave control unit 303 controls the opening and closing operations of the opening and closing unit 311 in accordance with the opening and closing operations corresponding to the manipulation input of the master grip 1.

When the interlock mode is switched to the interlock stop mode by the control signal 405, the transmission of the opening and closing command value 403A is stopped. Therefore, the operation of the opening and closing unit 311 is not controlled until the interlock stop mode is switched to the interlock mode by the control signal 405.

The control unit 400 has a device configuration of a computer that includes a CPU, a memory, an input and output interface, and an external storage device. A control program executing the above-described control functions is configured by the computer.

Next, an operation of the master-slave manipulator 500 according to this embodiment will be described focusing on the control operation of the opening and closing unit 311 performed by the master grip 1.

Figure 4:
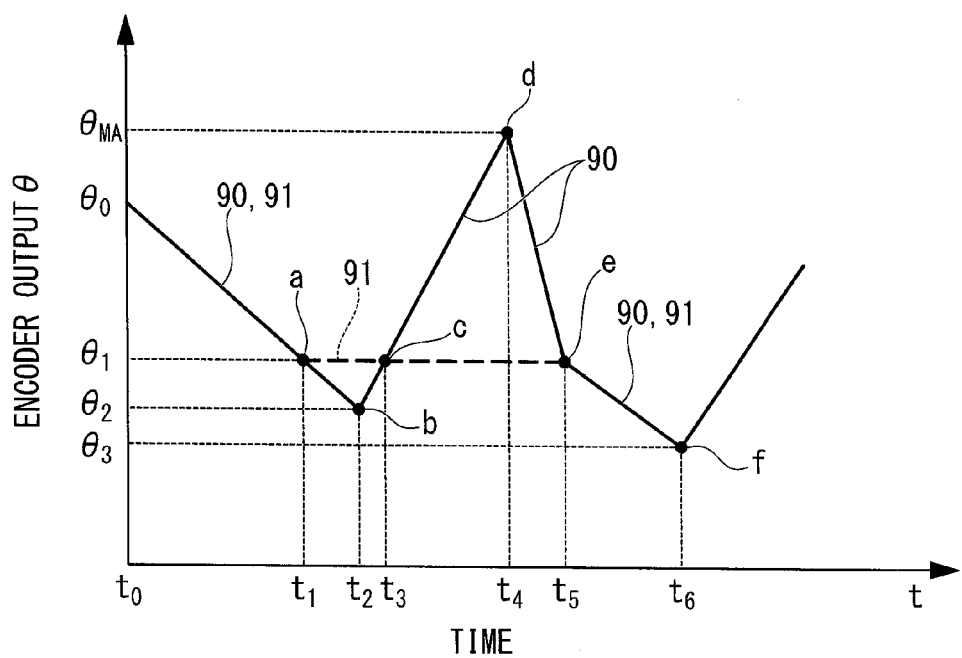
FIG. 4 is a graph schematically illustrating an example of an operation of the manipulator system according to the embodiment of the present invention.
Figure 7A:
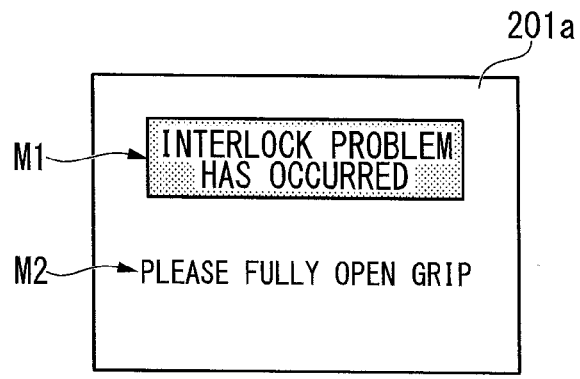
FIG. 7A is a schematic diagram illustrating an example of a display screen of the manipulator system according to the embodiment of the present invention.
Figure 7B:
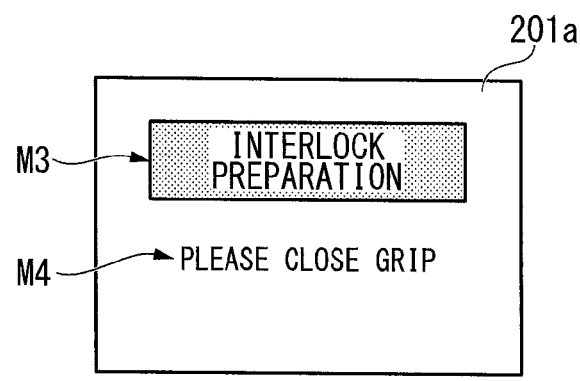
FIG. 7B is a schematic diagram illustrating an example of a display screen of the manipulator system according to the embodiment of the present invention.
Figure 7C:
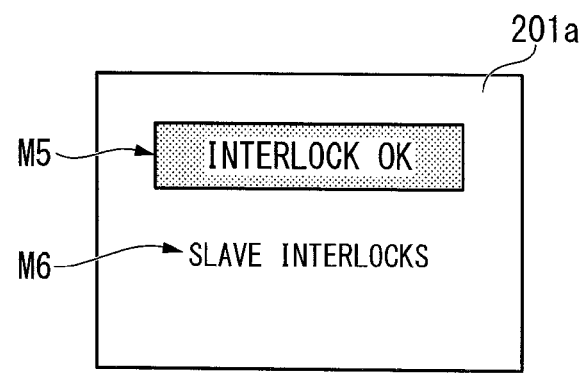
FIG. 7C is a schematic diagram illustrating an example of a display screen of the manipulator system according to the embodiment of the present invention.

FIG. 4 is a graph schematically illustrating an example of an operation of the manipulator system according to this embodiment of the present invention. In FIG. 4, the horizontal axis represents a time t. In FIG. 4, the vertical axis represents an encoder output θ. FIGS. 5A1 to 5C2 are diagrams illustrating the operation of the manipulator system according to this embodiment of the present invention. FIGS. 6A1 to 6C2 are diagrams illustrating the operation of the manipulator system continued from FIGS. 5A1 to 5C2 according to this embodiment of the present invention. In FIGS. 5A1 to 6C2, A1, B1, and C1 indicate the operation of the master manipulator unit. In FIGS. 5A1 to 6C2, A2, B2, and C2 indicate the operation of the opening and closing unit 311. FIGS. 7A to 7C are schematic diagrams illustrating examples of display screens of the manipulator system according to the embodiment of the present invention.

First, a normal operation of the master-slave manipulator 500 will be simply described.

In the master-slave manipulator 500, as shown in FIG. 1, the operator Op gripping the master grips 203L and 203R is able to perform manipulation to change the positions or orientations of the master grips 203L and 203R while viewing the display unit 201. Then, the output signal of the encoder from each movable unit of the master arm 202 is transmitted to the master control unit 401.

The master control unit 401 analyzes the output signal, generates the driving command value 403 of each movable unit of the slave arm 301 used to drive the slave manipulator 300 so as to correspond to the position and orientation of each of the master grips 203L and 203R, and then transmits the driving command value 403 to the manipulator control unit 402.

The manipulator control unit 402 converts the transmitted driving command value 403 into a driving signal of the slave arm 301, and then transmits the converted driving signal to the slave control unit 303. Thus, the driving of the slave arm 301 is controlled, and the position and orientation of the distal end of the treatment tool 302 are controlled to correspond to the position and orientation of each of the master grips 203L and 203R.

On the other hand, the operator Op also manipulates the manipulation handles 1b of the master grips 203L and 203R to change the opening and closing angle in parallel, as necessary. The spring 3 is installed in each of the master grips 203L and 203R. Thus, when the manipulation handles 1b are closed, the spring 3 is deformed and the elastic restoring force is generated in proportion to the amount of deformation. Therefore, the operator Op manipulating the manipulation handles 1b feels the manipulation resistance in his or her hands.

When the manipulation handles 1b are manipulated, the output signal 4a of the encoder 4 of each of the master grips 203L and 203R is transmitted to the master control unit 401.

The master control unit 401 generates the opening and closing command value 403A corresponding to the driving signal of the opening and closing driving unit 313 which is a movable unit opening and closing the opening and closing unit 311 installed at the distal end of the treatment tool 302 based on the output signal 4a from each encoder 4 and transmits the opening and closing command value 403A to the slave control unit 303 together with the movable unit selection signal 404 corresponding to the opening and closing driving unit 313. Thus, the driving of the opening and closing driving unit 313 is controlled and the opening and closing angle of the opening and closing unit 311 of the treatment tool 302 is controlled to correspond to the opening and closing angle of the manipulation handles 1b.

Therefore, the opening and closing unit 311 is able to grip a grip object or cancel the gripping.

Thus, the operator Op performs a surgical operation by remotely manipulating the slave manipulator 300 using the master input section 200.

Next, an operation when the opening and closing operations of the opening and closing units 311 are not controlled appropriately using the master grips 203L and 203R will be described.

Since both the master grips 203L and 203R are configured by the master grip 1, a relation between the master grip 1 and the opening and closing unit 311 will be described below.

To facilitate the description, a case in which the correspondence relation is controlled such that the opening and closing angle $\theta_M$ of the manipulation handles 1b is the same as the opening and closing angle $\theta_S$ of the opening and closing unit 311 will be described.

The output signal 4a of the encoder 4 and the output signal 314a of the encoder 314 represent the values of the opening and closing angle. That is, the encoder outputs θ of the encoders 4 and 314 represent the opening and closing angles θ of the manipulation handles 1b and the opening and closing unit 311.

Various reasons why the opening and closing operations of the opening and closing units 311 do not interlock with the opening and closing operations of the master grip 1 are considered. However, when an operation deviated from the manipulation input continues, exact opening and closing operations are not performed and this operation affects a task performed using the opening and closing unit 311. For this reason, the master control unit 401 normally monitors the opening and closing operations of the opening and closing unit 311. When the opening and closing angle is deviated by a value equal to or greater than the allowance value, the master control unit 401 switches the mode to the interlock stop mode in accordance with the control signal 405.

This status frequently occurs when a grip object is gripped. For example, since the operator Op performs remote manipulation, the operator Op has no sufficient information on the size or hardness of the grip object. For example, when the grip object is sufficiently hard but the manipulation handles 1b are closed by the opening and closing angle less than an angle corresponding to the size of the grip object, the opening and closing unit 311 may not be closed by the opening and closing angle corresponding to the opening and closing command value 403A. Thus, the opening and closing angle of the manipulation handles 1b may be different from the opening and closing angle of the opening and closing unit 311. Further, when the grip object is deformed, but the resistance is large and the closing speed is too fast, the opening and closing unit 311 may not close to the opening and closing angle corresponding to the opening and closing command value 403A.

It is assumed that the manipulation handles 1b are closed from the open state in which the manipulation handles 1b and the opening and closing unit 311 are opened by an angle of $\theta_0$ (where $\theta_0 < \theta_{MA}$) at time $t_0$ (hereinafter, a subscript n of time $t_n$ indicates a temporal sequence wherein a larger number subscript indicates a later time) and the opening and closing unit 311 grips a flexible grip object W (see FIG. 5A2) shown in FIG. 5A2.

As shown in FIG. 4, the encoder output θ of the encoders 4 and 314 gradually decreases from $\theta_0$ over time, as in polygonal lines 90 and 91. Here, since the manipulation handles 1b interlock with the opening and closing unit 311, the polygonal lines 90 and 91 overlap each other.

Further, the change in the encoder output indicated by the polygonal lines is merely an example. A manipulation input indicating the change in an appropriate curve shape can be performed by a manipulation method of the manipulation handles 1b.

As shown in FIG. 4, it is assumed that the opening and closing unit 311 is not closed in response to a manipulation input at time $t_1$ ($\theta = \theta_1$, where $\theta_1 < \theta_0$) when the opening and closing unit 311 grips the grip object W (see FIG. 5A1 and FIG. 5A2).

In this case, after time $t_1$ when the polygonal lines 90 and 91 are branched at point a of FIG. 4, the encoder output θ of the encoder 4 decreases, as indicated by the polygonal line 90. However, the encoder output θ of the encoder 314 remains "$\theta = \theta_1$," as indicated by the polygonal line 91 (see a heavy dashed line in the drawing).

When the master control unit 401 detects that the opening and closing angle is deviated by a value equal to or greater than the allowance value immediately after time the master control unit 401 transmits the control signal 405 to the manipulator control unit 402 and switches the mode to the interlock stop mode. Thus, even when the operator Op opens or closes the manipulation handles 1b, the opening and closing command value 403A corresponding to the opening or closing operation is not transmitted from the manipulator control unit 402 to the slave control unit 303.

Therefore, the opening and closing driving unit 313 stops at the opening and closing angle when entering the interlock stop mode.

When the mode is switched to the interlock stop mode, the master control unit 401 displays a warning display M1 (for example, "Interlock problem has occurred") indicating that an interlock problem has occurred and a guidance display M2 (for example, "Please fully open grip") explaining a countermeasure method for the operator Op on a display screen 201a of the display unit 201, as in FIG. 7A.

When the operator Op views the guidance display M2 and opens the manipulation handles 1b from time $t_2$, as in FIG. 4 (see FIG. 5B1), the encoder output θ of the encoder 4 gradually increases from $\theta_2$ (where $\theta_2 < \theta_1$) to $\theta_{MA}$.

At this time, at time $t_3$, the encoder output of the encoder 4 becomes $\theta_1$ (see point c), and thus coincides with the encoder output of the encoder 314.

In this case, since the position detection switch 6 does not detect the manipulation handles 1b and the interlock permission mode signal 6a is not generated, the interlock permission mode is not set. Further, the master control unit 401 detects the change in the opening and closing angle of the manipulation handles 1b in the opening direction from the change in the output signal 4a.

Therefore, in this embodiment, the master control unit 401 does not switch the mode to the interlock mode. Even when the encoder output of the encoder 4 increases, the opening and closing unit 311 does not interlock and the encoder output of the encoder 314 remains "θ=θ$_1$." That is, the opening and closing unit 311 is not opened through the manipulation input of the manipulation handles 1b (see FIG. 5B2).

At time t$_4$, the operator Op opens the manipulation handles 1b up to the maximum opening and closing angle (see point d of FIG. 4). At this time, as shown in FIG. 5C1, one of the manipulation handles 1b is located at the position detection position of the position detection switch 6. Therefore, the position detection switch 6 transmits the interlock permission mode signal 6a to the master control unit 401. Thus, the interlock permission mode starts.

As shown in FIG. 7B, the master control unit 401 enters the interlock permission mode and informs the operator Op that the interlock problem is resolved. Therefore, the master control unit 401 displays an information display M3 (for example, "Interlock preparation") and a guidance display M4 (for example, "Please close grip") explaining the countermeasure method for the operator Op on the display screen 201a of the display unit 201.

Since the operator Op views the display message on the display unit 201, as in FIG. 7B, and knows that the interlock starts through the next manipulation, the operator Op can prepare manipulation when the interlock starts.

The operator Op views the guidance display M4 and gradually closes the manipulation handles 1b. Thus, the encoder output θ of the encoder 4 gradually decreases from θ$_{M4}$ to θ$_1$.

At this time, at time t$_5$, the encoder output of the encoder 4 is θ$_1$ (see point e), and thus coincides with the encoder output of the encoder 314 (see FIG. 6A1 and FIG. 6A2).

In this case, since the interlock permission mode is set, the master control unit 401 detects the change in the opening and closing angle of the manipulation handles 1b in the closing direction from the change in the output signal 4a.

Therefore, the master control unit 401 transmits the control signal 405 to the manipulator control unit 402 and switches the interlock stop mode to the interlock mode.

Further, as shown in FIG. 7C, the master control unit 401 enters the interlock mode and displays an information display M5 (for example, "Interlock OK") and a detailed information display M6 (for example, "Slave interlocks") on the display unit 201 to inform the operator Op that the interlock problem is resolved.

Thus, after the interlock with the opening and closing unit 311 restarts, the opening and closing angle of the opening and closing unit 311 is changed together with the opening and closing angle of the manipulation handles 1b.

Thus, the operator Op can continue manipulation scheduled to be performed from time t$_1$, for example, the operator Op can continue manipulation to close the manipulation handles and further grip the grip object W (see FIG. 6B1 and FIG. 6B2 and a straight line ef in FIG. 4).

Further, the operator Op can open the manipulation handles 1b to cancel gripping the grip object W, as necessary (see FIG. 6C1 and FIG. 6C2). In this case, since the operator Op understands that the interlock restarts and then opens the manipulation handles 1b, the operator Op can react accordingly by adjusting the opening speed without a sudden drop of the grip object W or moving the master grip 1 and manipulating the master arm 202, for example, to move the opening and closing unit 311 to a position at which the cancellation of the gripping is suitable and perform cancelling of the gripping.

Thus, since the master-slave manipulator 500 includes the position detection switch 6 as the interlock permission input unit which the operator Op can manipulate, it is possible to prevent the interlock operation from being performed at an unexpected timing. Therefore, when an operation of the opening and closing unit 311 is deviated from an operation corresponding to a manipulation input of the master grip 1, workability of the opening and closing unit 311 can be improved.

[First Modified Example]

Next, a first modified example of the embodiment will be described.

Figure 8:
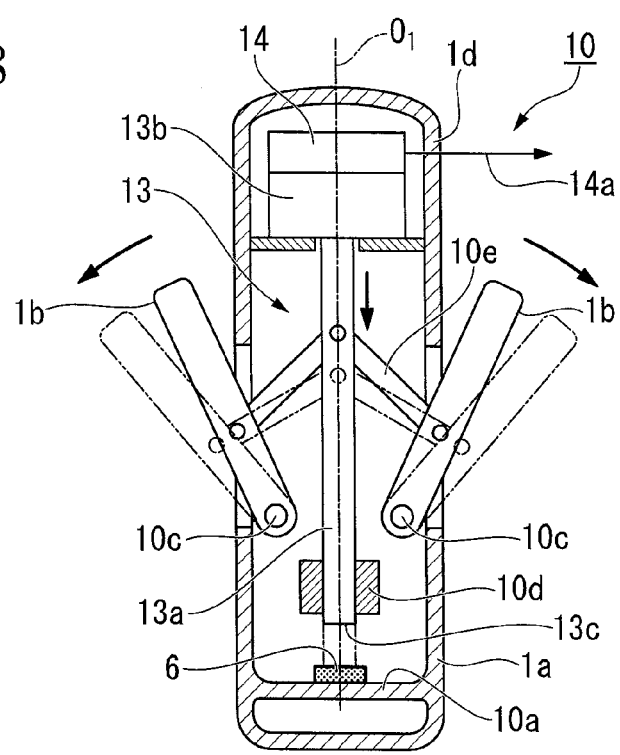
FIG. 8 is a schematic sectional view illustrating a master manipulation unit of a manipulator system according to a first modified example of the embodiment of the present invention.

FIG. 8 is a schematic sectional view illustrating a master manipulation unit of a manipulator system according to the first modified example of the embodiment of the present invention.

The master grip 1 according the above-described embodiment has the configuration in which the position detection switch 6 detects the positions of the manipulation handles 1b and the interlock permission mode signal 6a is generated. However, a master grip 10 (master manipulation unit) according to the first modified example in FIG. 8 detects a position of a member (a moving shaft 13a to be described below) that linearly moves in interlock with manipulation handles 1b. In the first modified example, a grip unit 1a has a position detection switch 6 therein.

The master grip 10 according to the first modified example can be used as the master grips 203L and 203R of the master-slave manipulator 500, as in the master grip 1 according to the above-described embodiment.

Hereinafter, differences between the first modified example and the above-described embodiment will mainly be described.

The master grip 10 according to the first modified example includes rotation shafts 10c, an actuator 13, and an encoder 14 (master angle detection unit) instead of the rotation shaft 1c, the spring 3, and the encoder 4 of the master grip 1 according to the above-described embodiment.

The rotation shaft 10c rotatably holds the end of the manipulation handle 1b instead of the rotation shaft 1c according to the above-described embodiment. The rotation shafts 10c are disposed on either side of an opening and closing central axial line O$_1$ inside the grip unit 1a at symmetrical positions with respect to the opening and closing central axial line O$_1$. The rotation shafts 10c hold the ends of the manipulation handles 1b at the two positions.

The actuator 13 is configured to open and close the manipulation handles 1b symmetrically with respect to the opening and closing central axial line O$_1$ and generate manipulation resistance as the manipulation handles 1b are manipulated.

The actuator 13 includes the moving shaft 13a that linearly moves along the opening and closing central axial line O$_1$ and a resistance generation unit 13b that movably holds a first end of the moving shaft 13a and generates a resistant force in a direction opposite to the movement direction.

A second end of the moving shaft 13a is held to be linearly moved by a slide guide 10d that is installed inside on the proximal end side (the side closer to the grip unit 1a) of a casing unit 1d.

A distal end 13c at the second end of the moving shaft 13a protrudes to be suitable to the proximal end side of the casing unit 1d from a slide guide 10d.

Links 10e that transmit rotation movement of the manipulation handles 1b about the rotation shafts 10c to the moving shaft 13a and linearly move the moving shaft 13a are connected between the middle portion of the moving shaft 13a and the manipulation handles 1b, respectively. Thus, since the opening and closing angle of the manipulation handles 1b and the amount of movement of the moving shaft 13a have a one-to-one relation, the opening and closing angle of the manipulation handles 1b can be detected from the amount of movement of the moving shaft 13a.

In the grip unit 1a, a holding plate 10a on which a position detection switch 6 is disposed is provided at a position more distant than the movement range of the distal end 13c to the front side of the distal end 13c of the moving shaft 13a.

The position detection switch 6 on the holding plate 10a is disposed at a position at which the position detection switch 6 can detect the position of the distal end 13c of the moving shaft 13a and determine whether the distal end 13c reaches the position corresponding to the maximum opening and closing angle of the manipulation handles 1b.

The resistance generation unit 13b includes an elastic member resisting the movement of the moving shaft 13a, such as an air spring or a spring member such as a spring. The resistance generation unit 13b is fixed to the internal unit on the distal end (opposite side to the grip unit 1a) of the casing unit 1d.

The encoder 14 detects the amount of movement of the moving shaft 13a of the actuator 13 and transmits an output signal 14a corresponding to the detected value to the master control unit 401. The encoder 14 is electrically connected to the master control unit 401 via a wiring (not shown).

The output signal 14a transmitted to the master control unit 401 is converted into an opening and closing angle of the manipulation handles 1b with reference to a conversion table or the like stored in advance in the master control unit 401.

In the master grip 10 according to the first modified example, when the operator Op performs manipulation to open the manipulation handles 1b at the maximum opening and closing angle, the position detection switch 6 can transmit the interlock permission mode signal 6a to the master control unit 401, as in the master grip 1 according to the above-described embodiment.

Accordingly, it is possible to prevent the interlock operation from being performed at an unexpected timing, as in the above-described embodiment. Therefore, when an operation of the opening and closing unit 311 is deviated from an operation corresponding to a manipulation input of the master grip 10, workability of the opening and closing unit 311 can be improved.

[Second Modified Example]

Next, a second modified example of the embodiment will be described.

Figure 9:
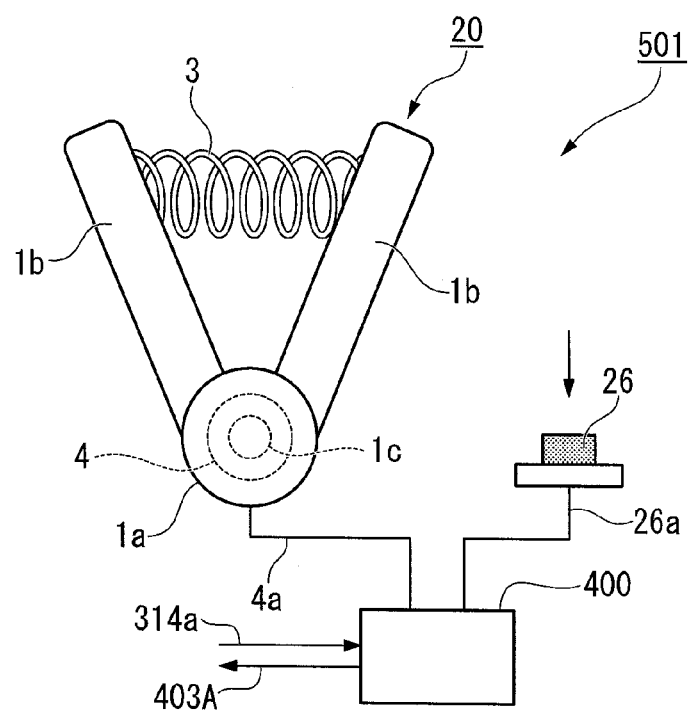
FIG. 9 is a schematic diagram illustrating main units of a manipulator system according to a second modified example of the embodiment of the present invention.

FIG. 9 is a schematic diagram illustrating main units of a manipulator system according to the second modified example of the embodiment of the present invention.

As shown in FIG. 9, a master-slave manipulator 501 (manipulator system) according to the second modified example includes a master grip 20 instead of the master grip 1 of the master-slave manipulator 500 according to the above-described embodiment and further includes an input switch 26 (interlock permission input unit).

Hereinafter, differences between the second modified example and the above-described embodiment will mainly be described.

The master grip 20 according to the second modified example does not include the holding arm member 5 and the position detection switch 6 of the master grip 1 according to the above-described embodiment.

The input switch 26 is separated from the master grip 20. When the operator Op manipulates the input switch 26 at an appropriate timing, the input switch 26 generates an interlock permission mode signal 26a used to enter the interlock permission mode and transmits the interlock permission mode signal 26a to the master control unit 401.

Therefore, the input switch 26 is electrically connected to the master control unit 401.

The configuration of the input switch 26 is not particularly limited, as long as the input switch 26 is an input switch that the operator Op can manipulate. For example, a button switch which the operator Op can manipulate with his or her hand or a footswitch which the operator Op can manipulate with his or her foot can be used appropriately.

In the master-slave manipulator 501 according to the second modified example, the interlock permission mode signal 26a can be generated at an appropriate timing through manipulation of the operator Op. Therefore, when the master control unit 401 detects an interlock problem, the interlock mode is switched to the interlock stop mode, as in the above-described embodiment. In the master-slave manipulator 501, for example, a message "Please manipulate the input switch when you are ready to restart interlocking" is displayed to prompt the operator Op to manipulate the input switch 26, instead of the guidance display M2 in FIG. 7A.

Thus, when the operator Op views the guidance display such as the warning display M1, the operator Op can understand that an interlock problem has occurred. Therefore, the operator Op can prepare to restart the interlocking, and then manipulate the input switch 26 to enter the interlock permission mode.

When entering the interlock permission mode, the master control unit 401 displays substantially the same screen display as the screen display of FIG. 7B. For example, a message "Please open and slowly close the grip when a problem occurs" is displayed as the guidance display M4.

Thus, the operator Op can open the manipulation handles 1b by an angle slightly less than the encoder output $\theta_1$ in FIG. 4 and manipulate the manipulation handles 1b to close the manipulation handles 1b from an appropriate opening and closing angle over point c. When the encoder output of the output signal 4a in the closing direction coincides with $\theta_1$, as in the above-described embodiment, the master control unit 401 switches the interlock stop mode to the interlock mode to restart the interlocking.

Thus, in the second modified example, the operator Op can restore the interlocking swiftly without opening the opening and closing angle of the manipulation handles 1b up to the maximum opening and closing angle.

Since the interlocking can restart merely by slightly opening the manipulation grip from the opening and closing angle in the occurrence of an interlocking problem and closing the manipulation grip, the interlocking can restart from substantially the same manipulation state as that in the occurrence of the interlocking problem. Therefore, a task can continue smoothly using the opening and closing unit 311.

In particular, when the footswitch is used as the input switch 26, the operator Op can manipulate the input switch 26 without completely removing his or her hand from the master grip 20. Accordingly, the task can continue smoothly.

[Third Modified Example]

Next, a third modified example of the embodiment will be described.

Figure 10:
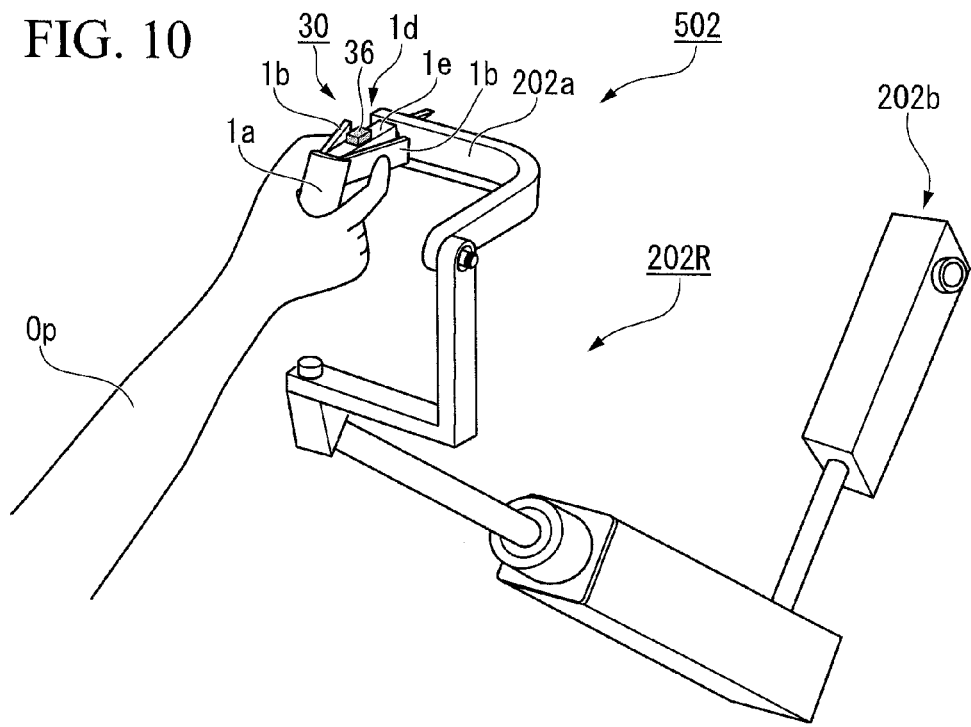
FIG. 10 is a schematic perspective view illustrating main units of a manipulator system according to a third modified example of the embodiment of the present invention.

FIG. 10 is a schematic sectional view illustrating main units of a manipulator system according to the third modified example of the embodiment of the present invention.

As shown in FIG. 10, a master-slave manipulator 502 (manipulator system) according to this modified example includes a master grip 30 instead of the master grip 1 of the master-slave manipulator 500 according to the above-described embodiment.

Hereinafter, differences between the third modified example and the above-described embodiment will mainly be described.

The master grip 30 according to the third modified example does not include the holding arm member 5 and the position detection switch 6 of the master grip 1 according to the above-described embodiment. Further, an input switch 36 (interlock permission input unit) is disposed on the surface of the casing unit 1d. That is, the master grip 30 has a configuration in which the input switch 36 is added to the master grip 20 according to the above-described second modified example.

When the operator Op manipulates the input switch 36 at an appropriate timing, the master grip enters the interlock permission mode. Therefore, the input switch 36 generates the same interlock permission mode signal 26a as that of the second modified example and transmits the interlock permission mode signal 26a to the master control unit 401 (not shown in FIG. 10). Therefore, the input switch 36 is electrically connected to the master control unit 401.

The input switch 36 may be disposed at any position of the surface of the casing unit 1d at which the operator Op can manipulate the input switch 36. In the third modified example, the input switch 36 is preferably disposed at a position at which the operator Op can manipulate the input switch 36 with some of his or her fingers while gripping the grip unit 1a to perform a manipulation input.

For example, as shown in FIG. 10, the input switch 36 can be disposed on an upper surface 1e of the casing unit 1d on the upper side when the operator Op grips the grip unit 1a. In this case, for example, the operator Op can manipulate the input switch 36 by moving his or her forefinger upward. At this time, the operator Op can manipulate the other manipulation handle 1b with his or her thumb and hold the opening and closing angle of the manipulation handle 1b at the opening and closing angle in the occurrence of the interlock problem, even after removing his or her forefinger.

The configuration of the input switch 36 is not particularly limited, as long as the input switch 36 is an input switch that the operator OP can manipulate. For example, a button switch that the operator Op can manipulate with his or her hand can be used appropriately.

In the master-slave manipulator 502 according to the third modified example, the operator Op can restore the interlocking swiftly without opening the opening and closing angle of the manipulation handles 1b up to the maximum opening and closing angle, as in the master-slave manipulator 501 according to the second modified example. Accordingly, since the interlocking can restart from substantially the same manipulation state as the state in the occurrence of the interlocking problem, a task can continue smoothly using the opening and closing unit 311.

In particular, the input switch 36 is disposed on the surface of the casing unit 1d. Therefore, even when the operator Op grips the grip unit 1a, the operator Op can easily manipulate the input switch 36. Accordingly, the task can continue smoothly.

[Fourth Modified Example]

Next, a fourth modified example of the embodiment will be described.

Figure 11:
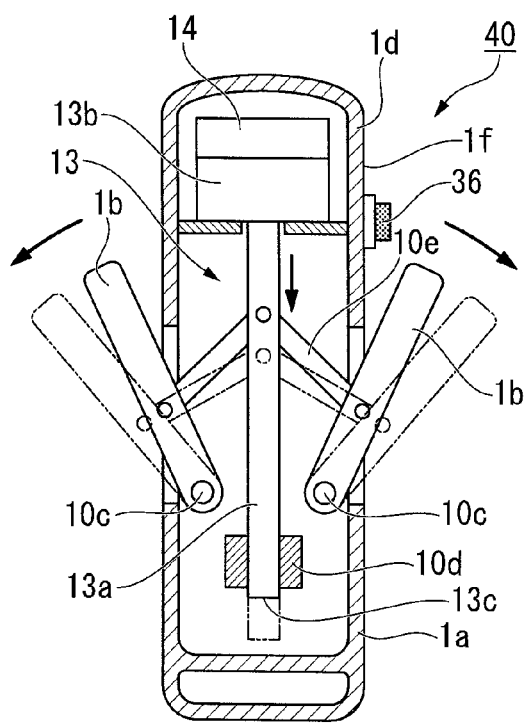
FIG. 11 is a schematic sectional view illustrating a master manipulation unit of a manipulator system according to a fourth modified example of the embodiment of the present invention.

FIG. 11 is a schematic sectional view illustrating a master manipulation unit of a manipulator system according to the fourth modified example of the embodiment of the present invention.

As shown in FIG. 11, a master grip 40 according to the fourth modified example excludes the position detection switch 6 from the master grip 10 according to the first modified example. Further, the input switch 36 according to the third modified example is disposed on a side surface if of the casing unit 1d.

As in the master grip 1 according to the above-described embodiment, the master grip 40 according to the fourth modified example can be used as the master grips 203L and 203R of the master-slave manipulator 500.

Hereinafter, differences between the fourth modified example, and the above-described embodiment and the first modified example will mainly be described.

In the fourth modified example, the input switch 36 is disposed at a position on the side surface 1f on which the manipulation handle 1b which the operator Op manipulates with his or her forefinger is disposed when the operator Op grips the grip unit 1a and at a position on the side of the distal end of the casing unit 1d more than the distal end of the manipulation handle 1b.

Therefore, the operator Op can manipulate the input switch 36 by moving his or her forefinger to the distal end of the casing unit 1d. At this time, even in the fourth modified example, the operator Op can manipulate the other manipulation handle 1b with his or her thumb. The operator Op can hold the opening and closing angle of the manipulation handle 1b at the opening and closing angle when an interlock problem occurs, even after removing his or her forefinger.

In the master grip 40 according to the fourth modified example, the operator Op can restore the interlocking swiftly without opening the opening and closing angle of the manipulation handles 1b up to the maximum opening and closing angle, and thus start the interlocking from substantially the same manipulation state as that in the occurrence of an interlock problem. Accordingly, as in the third modified example, a task can continue smoothly using the opening and closing unit 311.

In the embodiment and the modified examples described above, the cases in which the master manipulator unit performs the opening and closing manipulations of the slave motion unit have been described. However, the manipulation input of the master manipulation unit is not limited to the opening and closing manipulation. For example, when the slave motion unit linearly moves and grips an object, a manipulation input of the linear movement may be performed.

In the embodiment and the modified examples described above, the cases in which the opening and closing are performed bilaterally symmetrically with respect to the opening and closing central axial line when the master manipulation unit performs the opening and closing manipulations of the slave motion unit have been described. However, the opening and closing may be performed asymmetrically with respect to an appropriate axial line. Further, one of a pair of manipulation members or one of a pair of treatment tool pieces may be moved to the other thereof so that the opening and closing are performed.

In the embodiment and the modified examples described above, the cases in which the interlock control unit interlocks the slave motion unit with an operation corresponding to the manipulation input when the interlock control unit receives the interlock permission mode signal, and then the detection value of the opening and closing angle of the manipulation member corresponds to the detection value of the opening and closing angle of the opening and closing motion unit and the detection value of the opening and closing angle of the manipulation member is changed in the closing direction of the manipulation member have been described.

In this configuration, when the interlocking restarts, the manipulation member is moved in the closing direction. Therefore, a grip object is not dropped erroneously.

The interlock permission mode is started by the interlock permission mode signal generated by the interlock permission input unit through the manipulation of the operator Op. Therefore, since the operator Op expects the restart timing of the interlocking, the operator Op can prepare to perform a manipulation input for the interlock restart. Accordingly, even when the opening and closing unit 311 is gradually opened after the interlock start, the probability that a grip object is erroneously dropped is considerably low compared to a case in which the interlocking is not expected and the interlock restart is not prepared for.

Accordingly, the interlock control unit is capable of interlocking the slave motion unit with an operation corresponding to the manipulation input when the interlock control unit receives the interlock permission mode signal, and then the detection value of the opening and closing angle of the manipulation member corresponds to the detection value of the opening and closing angle of the opening and closing motion unit and the detection value of the opening and closing angle of the manipulation member is changed in the opening direction of the manipulation member.

In this case, since the opening and closing unit 311 is moved in the opening direction immediately after the interlock restart, no pressure force is applied to a grip object. Accordingly, it is possible to prevent the grip object from being deformed.

Further, the interlock control unit is capable of interlocking the slave motion unit with an operation corresponding to the manipulation input after the interlock control unit receives the interlock permission mode signal, when the detection value of the opening and closing angle of the manipulation member corresponds to the detection value of the opening and closing angle of the opening and closing motion unit, as well as the detection value of the opening and closing angle of the manipulation member is changed in the opening or closing direction of the manipulation member. Furthermore, the interlock control unit is capable of selecting between the interlock of the case in which the detection value is changed in the opening direction and the interlock of the case in which the detection value is changed in the closing direction.

In this case, immediately before the operator Op starts a task, the operator Op can select an interlock start condition in the opening direction of the manipulation member or the closing direction of the manipulation member in accordance with a kind or characteristics of the grip object. Therefore, since the interlocking can be restarted in accordance with the kind or characteristics of the grip object, workability can be improved even when an interlock problem occurs.

In the embodiment and the modified examples described above, the cases in which the master control unit 401 displays a message on the display unit 201 to notify the operator Op of occurrence of an interlock problem, the switching to the interlock permission mode, the interlock restart, and the like have been described. However, the operator Op may be notified through sound or voice.

In the embodiment and the modified examples described above, the cases in which the manipulation member is not opened to the maximum opening and closing angle when the spring 3 is in the natural state, and the position detection switch 6 is pressed when the spring 3 is extended further from the natural state have been described. However, the present invention is not limited to the spring 3 installed in this way.

For example, when the spring 3 is in the natural state, the manipulation member may be opened to the maximum opening and closing angle and the position detection switch 6 may be pressed.

Figure 12A:
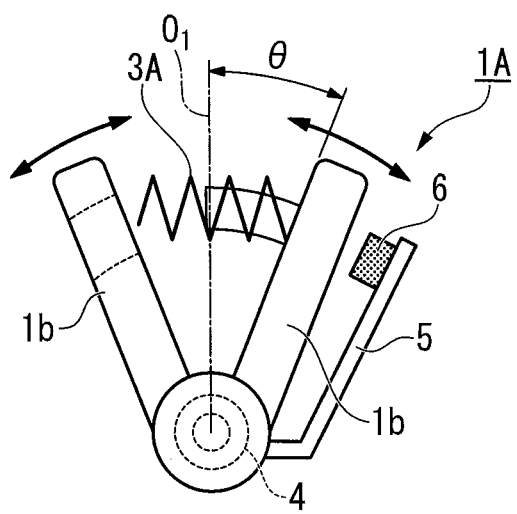
FIG. 12A is a schematic diagram illustrating the configuration of a spring of a master manipulation unit of a modified example (fifth modified example) applicable to the embodiment and each modified example of the present invention.
Figure 12B:
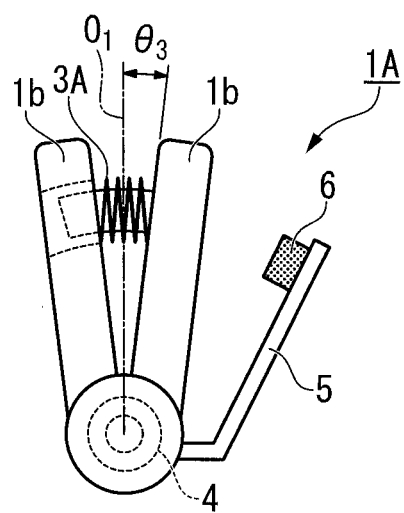
FIG. 12B is a schematic diagram illustrating the configuration of the spring of the master manipulation unit of a modified example (fifth modified example) applicable to the embodiment and each modified example of the present invention.

The configurations shown in FIGS. 12A and 12B may be realized. FIGS. 12A and 12B are schematic diagrams illustrating the configuration of a master manipulation unit according to a modified example (a fifth modified example) applicable to the embodiment and the modified examples described above.

A master grip 1A (master manipulation unit) according to this modified example (the fifth modified example) includes a spring 3A instead of the spring 3 of the master grip 1 according to the above-described embodiment. A first end portion (the right side of the drawing) of the spring 3A is fixed to the inside of the manipulation handle 1b in a first direction (the right side of the drawing) and a second end portion (the left side of the drawing) of the spring 3A faces the manipulation handle 1b in a second direction to come into contact with and be separated from the manipulation handle 1b.

Thus, when the manipulation handles 1b are closed up to an opening and closing angle corresponding to a value equal to or less than the length of the spring 3A in the natural state, as in FIG. 12B, the elastic restoring force of the spring 3A is generated and the manipulation resistance thus occurs. Further, when the manipulation handles 1b are opened up to an opening and closing angle corresponding to a value equal to or greater than the length of the spring 3A in the natural state, as in FIG. 12A, the manipulation resistance generated by the spring 3A does not occur.

In this configuration, no manipulation resistance occurs when the position detection switch 6 is pressed. Therefore, the position detection switch 6 can be pressed swiftly by a small force.

All of the constituent elements described in the embodiment and the modifications may be appropriately combined or deleted.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A manipulator system comprising:
   a master manipulation unit with which an operator performs a manipulation input;
   a slave motion unit that is configured to operate in accordance with the manipulation input;
   an interlock control unit that analyzes the manipulation input and performs control to operate the slave motion unit, interlocking with the manipulation input; and
   an interlock permission input unit that is configured to be manipulated by the operator and transmits, to the interlock control unit, an interlock permission mode signal used to enter a mode in which interlock of the slave motion unit is permitted based on the manipulation input of the mater manipulation unit when the operator manipulates the interlock permission input unit,
   wherein the interlock control unit stops the interlock control when the operation of the slave motion unit is deviated from an operation corresponding to the manipulation input, and monitors the manipulation input of the master manipulation unit and an operation state of the slave motion unit, and
   the interlock control unit interlocks the operation of the slave motion unit with the operation corresponding to the manipulation input after the interlock control unit receives the interlock permission mode signal, when the interlock control unit detects that the manipulation input matches the operation state.

2. The manipulator system according to claim 1,
wherein the master manipulation unit includes:
a manipulation member that is provided to be opened and closed in order to perform the manipulation input; and
a master angle detection unit that detects an opening and closing angle of the manipulation member and transmits a detection value of the opening and closing angle of the manipulation member to the interlock control unit,
the slave motion unit includes:
an opening and closing motion unit that is provided to be opened and closed; and
a slave angle detection unit that detects an opening and closing angle of the opening and closing motion unit and transmits a detection value of the opening and closing angle of the opening and closing motion unit to the interlock control unit, and
the interlock control unit interlocks the slave motion unit with an operation corresponding to the manipulation input after the interlock control unit receives the interlock permission mode signal, when the detection value of the opening and closing angle of the manipulation member corresponds to the detection value of the opening and closing angle of the opening and closing motion unit, as well as when the detection value of the opening and closing angle of the manipulation member is changed in a closing direction of the manipulation member.

3. The manipulation system according to claim 1, further comprising:
an information display unit that displays information transmitted from the interlock control unit,
wherein the interlock control unit that displays restart of interlock with the information display unit after the interlock control unit receives the interlock permission mode signal, when the interlock control unit detects that the slave motion unit interlocks with the operation corresponding to the manipulation input.

4. The manipulator system according to claim 2, wherein the interlock permission input unit is configured by a position detection switch that detects that the manipulation member is moved to a maximum opening position and generates the interlock permission mode signal.

5. The manipulator system according to claim 2, wherein the interlock permission input unit is configured by an input switch provided on a surface of the master manipulation unit.

6. The manipulator system according to claim 2, wherein the interlock permission input unit is configured by an input switch that is provided separately from the master manipulation unit.

7. The manipulator system according to claim 6, wherein the input switch is configured by a footswitch.

8. The manipulator system according to claim 1,
wherein the master manipulation unit includes:
a manipulation member that is provided to be opened and closed in order to perform the manipulation input; and
a master angle detection unit that detects an opening and closing angle of the manipulation member and transmits a detection value of the opening and closing angle of the manipulation member to the interlock control unit,
the slave motion unit includes:
an opening and closing motion unit that is provided to be opened and closed; and
a slave angle detection unit that detects an opening and closing angle of the opening and closing motion unit and transmits a detection value of the opening and closing angle of the opening and closing motion unit to the interlock control unit, and
the interlock control unit interlocks the slave motion unit with an operation corresponding to the manipulation input after the interlock control unit receives the interlock permission mode signal, when the detection value of the opening and closing angle of the manipulation member corresponds to the detection value of the opening and closing angle of the opening and closing motion unit, as well as when the detection value of the opening and closing angle of the manipulation member is changed in an opening direction of the manipulation member.

9. The manipulator system according to claim 1,
wherein the master manipulation unit includes:
a manipulation member that is provided to be opened and closed in order to perform the manipulation input; and
a master angle detection unit that detects an opening and closing angle of the manipulation member and transmits a detection value of the opening and closing angle of the manipulation member to the interlock control unit,
the slave motion unit includes:
an opening and closing motion unit that is provided to be opened and closed; and
a slave angle detection unit that detects an opening and closing angle of the opening and closing motion unit and transmits a detection value of the opening and closing angle of the opening and closing motion unit to the interlock control unit, and
the interlock control unit is configured to interlock the slave motion unit with an operation corresponding to the manipulation input after the interlock control unit receives the interlock permission mode signal, when the detection value of the opening and closing angle of the manipulation member corresponds to the detection value of the opening and closing angle of the opening and closing motion unit, as well as when the detection value of the opening and closing angle of the manipulation member is changed in an opening or closing direction of the manipulation member, and the interlock control unit is configured to select between the interlock of the case in which the detection value is changed in the opening direction and the interlock of the case in which the detection value is changed in the closing direction.

* * * * *